United States Patent [19]

Farrell et al.

[11] Patent Number: 5,058,032

[45] Date of Patent: Oct. 15, 1991

[54] APPARATUS AND METHOD FOR MONITORING A WATER TREATMENT SYSTEM

[75] Inventors: Michael D. Farrell, Brookfield; Terry F. Teach, New Berlin, both of Wis.; John N. Evers, Fridley, Minn.

[73] Assignee: Autotrol Corporation, Milwaukee, Wis.

[21] Appl. No.: 425,239

[22] Filed: Oct. 23, 1989

[51] Int. Cl.$^5$ .............................................. G06F 15/20

[52] U.S. Cl. ..................................... 364/510; 364/500

[58] Field of Search .................. 364/510, 500, 551.01, 364/556, 558; 379/47, 50, 40, 42; 210/87, 143, 96.1

[56] References Cited

U.S. PATENT DOCUMENTS

| | | | |
|---|---|---|---|
| 3,159,573 | 12/1964 | Ritchie | 210/96.1 |
| 3,176,844 | 4/1965 | Nelson | 210/96.1 |
| 3,246,759 | 4/1966 | Matlon | 210/96.1 |
| 3,567,864 | 3/1971 | Palmer et al. | 379/40 |
| 3,676,336 | 7/1972 | O'Brien et al. | 210/96.2 |
| 4,401,976 | 8/1983 | Stadelmayr | 367/94 |
| 4,486,625 | 12/1984 | Reinauer et al. | 379/40 |
| 4,659,459 | 4/1987 | O'Leary et al. | 210/87 |
| 4,762,611 | 8/1988 | Schipper | 210/96.2 |
| 4,764,271 | 8/1988 | Acosta | 210/96.1 |
| 4,830,757 | 5/1989 | Lynch et al. | 364/500 |
| 4,873,648 | 11/1989 | Mouser et al. | 364/510 |
| 4,887,291 | 12/1989 | Stillwell | 379/50 |

*Primary Examiner*—Parshotam S. Lall

*Assistant Examiner*—Ellis B. Ramirez

*Attorney, Agent, or Firm*—Jansson & Shupe

[57] ABSTRACT

A monitoring apparatus for carrying out the method is connectable by a telephone line to a central computer system. The apparatus includes first and second input ports for receiving first and second signals, respectively. The first signal represents a volumetric water flow rate while the second signal represents a physical characteristic of the treated water. A processing circuit is connected to the input ports and includes a microprocessor programmable for receiving and totalizing the first signals to a flow volume. The processing circuit also includes a real time clock connected to the microprocessor for continuously computing time. A power supply provides the necessary voltages to the apparatus.

The apparatus is arranged to initiate a call to the central computer system upon the occurrence of any one of two or more described conditions such as measured deterioration of water quality, lapse of time or others. Several embodiments are disclosed.

17 Claims, 12 Drawing Sheets

APPARATUS AND METHOD FOR MONITORING A WATER TREATMENT SYSTEM

FIELD OF THE INVENTION

This invention is related generally to the treatment of water and, more particularly, to an apparatus and method which uses a physical characteristic of the water to monitor a water treatment system.

BACKGROUND OF THE INVENTION

Certain processes such as kidney dialysis, industrial washing and the like often require a supply of water having a particular physical characteristic. For example, the water supply may be required to be free of a particular mineral or other substance, perhaps radioactive, may be required to have a certain pH or may be required to exhibit a certain conductivity characteristic. A common way in which such a supply of water is furnished to the user is to design a treatment system which is located at the site of use and which is configured to treat water to exhibit a particular characteristic.

An example of such a water treatment system is a portable exchange deionizing system which includes both cation and anion exchange tanks and, possibly, one or more mixed bed tanks. The resulting particularly pure water has a low conductivity, sometimes expressed as a high resistivity. Such systems may optionally include one or more additional tanks for particle removal. The ion exchange tanks must be replaced before or at the point at which their resin beds become depleted to the extent they are unable to provide water with the required physical characteristic. Such water treatment systems are usually supported by companies which contract with users for the purpose. These support companies often have a significant number of systems within a metropolitan area, often 50 or more, which must be reliably yet efficiently serviced.

The resulting infrastructure includes customers having treatment systems of widely varying treatment capacities and having usage rates which vary between users and from time to time with respect to a given user. Clearly, an efficient support organization will be able to schedule tank exchanges at or just prior to the time at which water quality reaches an unacceptable level. In addition, this organization will want to schedule such tank exchanges so as to permit planning of efficient service vehicle routes, to avoid unnecessarily frequent tank exchange and to avoid unacceptable deterioration of water quality as to any customer. The organization will also want the capability to centrally modify the monitoring parameters to recognize changing circumstances. The need for a central monitoring capability would be most inexpensively met by using an existing communication path.

One approach to a water treatment problem is reflected in Japanese Patent Document 85-034880/06. In the described system, the treatment medium, an adsorbent, is maintained on site and periodically fed into the treating tank. The amount of adsorbent which is introduced is computed based upon water flow rate and a comparison of an actual water quality parameter with a pre-determined quality parameter.

In U.S. Pat. No. 4,762,611, the described invention uses conductivity as the physical characteristic to be maintained. Conductivity measurements are made only during times at which the water is flowing, a feature used for battery conservancy reasons. Water conductivity is displayed to the user and it is assumed that the user can interpret the data.

In U.S. Pat. No. 3,676,336, the described system measures water conductivity at the input stage and also measures the volume of treated water flow. These parameters are periodically multiplied and totalized and when the total reaches a predetermined value, regenerated resin is provided. The system is incapable of using water volume alone as a replacement parameter nor is it capable of using measured conductivity alone for that purpose.

These systems have no doubt proven effective for their intended purpose. However, they have failed to appreciate the need for an apparatus and method which may be used to monitor a system capable of treating water for any one of several physical characteristics. They have also failed to appreciate how information related to a water treatment system may be used to efficiently manage the exchange of treatment tanks for each of a significant number of installations while yet avoiding replacement of such tanks at a frequency greater than necessary. Having failed to recognize the problem, they have likewise failed to present practical solutions.

An apparatus and method for monitoring a water treatment system which would provide information to permit highly efficient tank replacement while yet avoiding unacceptable deterioration of the key physical characteristic(s) of the treated water would be an important advance in the art.

OBJECTS OF THE INVENTION

It is an object of this invention to overcome some of the problems and shortcomings of the prior art. Another object of this invention is to provide an apparatus and method which employ a physical characteristic of the treated water as a parameter for system monitoring.

Still another object of this invention is to provide an apparatus and method which will facilitate efficient scheduling of tank replacement at the installed treatment systems.

Yet another object of this invention is to provide an apparatus and method which help avoid deterioration of water quality to an unacceptable level for any customer.

Another object of this invention is to provide an apparatus and method for monitoring a water treatment system where the system monitoring parameters may be readily modified by the servicing organization.

Still another object of the invention is to provide an apparatus and method for monitoring a water treatment system which accomplishes central monitoring using an existing communication path.

These and other important objects will be apparent from the descriptions of this invention which follow.

SUMMARY OF THE INVENTION

As will become apparent from the following description, the function of the apparatus and the practice of the method for monitoring a water treatment system depend in part upon the availability of certain signals, each one of which represents a particular system parameter. These signals are used to determine whether or not one of two or more conditions may exist. If so, certain responsive activity occurs as a result.

A monitoring apparatus for carrying out the method is connectable by a telephone line to a central computer The apparatus includes first and second input ports for receiving first and second signals, respectively. The first signal represents a volumetric water flow rate while the second signal represents a physical characteristic of the treated water. A processing circuit is connected to the input ports and includes a microprocessor programmable for receiving and totalizing the first signals to a flow volume. The processing circuit also includes a real time clock connected to the microprocessor for continuously computing time. A power supply provides the necessary voltages to the apparatus.

Initiation of Calls

In the preferred embodiments, the initiation of a call will be by use of telephone line connected between the apparatus and a central computer system. When a call is initiated, the apparatus will first sample the telephone line (by detecting a voltage state) to determine its status. If it is available, the apparatus will dial the telephone number of the central computer system ("CCS") which has been programmed into the microprocessor. Once communication with the computer system has been established, the entirety of data will be transmitted by the apparatus to the CCS. Following completion of this transmission, the CCS may download any new instructions to the apparatus which may have been entered by the system support organization. The call is then ended.

A preferred apparatus is arranged for initiating a call to the computer and transmitting a message signal to it upon the occurrence of either a first condition or a second condition. The first condition on which a call would be initiated would include the registry in the microprocessor of first signals representing a total water flow volume which is equal to a predetermined volume. The predetermined volume would be measured from the last defined event, the replenishment or replacement of the treating tanks for example. It would be selected to be equal to or slightly less than the nominal volume of water for which the tanks are capable of maintaining the desired physical characteristic before tank replacement is again needed. In a preferred apparatus, the physical characteristic is conductivity.

The second condition would be considered a fault and could include the coexistence of the first signal and a second signal which represents a conductivity value equal to a predetermined value. It is to be understood that this feature is more useful in systems such as shown in FIG. 1. If the system is of the recirculating type, recirculating movement of water is substantially continuous and the need for the first signal is negated. In those situations, the second condition would be coincident with the second signal.

The predetermined value of conductivity is selected to be equal to that nominal threshold value above which the treated water is considered unacceptable in quality. Initiation of a call upon the occurrence of such a second signal in coexistence with the first signal will help assure that water is flowing at the time the threshold conductivity value is detected. This helps prevent false conductivity measurements which might occur if the water was stagnant.

Another, highly preferred apparatus will be arranged to initiate a call to a central computer based upon any one of four conditions, two of which have been described above. A third condition includes the lapse of a predetermined time counted from an earlier event such as the replacement of treating tanks or counted from the time of the preceding time-based call. A call may also be initiated on a fourth condition, i.e., manual actuation at the time that the treatment tanks are exchanged. Such initiation will usually be by the person servicing the tanks. Yet another highly preferred apparatus will be able to initiate a call upon the occurrence of a fifth condition such as the termination of the second condition. That is, such a call would be initiated when, for example, conductivity reverts to an acceptable value.

Any one of a large number of message signal types could be sent by the apparatus in each such call. However, in one preferred embodiment of the apparatus, the message signal will include a first set of data which identifies the site location of the apparatus and a second set of data for determining the time at which the call was initiated. It is to be understood that time and date signals are also generated by the CCS. The inclusion of a time signal in the message signal sent by the apparatus will permit detection of whether the timekeeping functions of the apparatus and the CCS are sufficiently synchronized.

The message signal would also include a third set of data for determining the total volumetric flow of water since the last defined event, i.e., tank replacement and a fourth set of data representing the status, i.e., normal or fault condition, of that input port related to the physical characteristic of the water. In other highly preferred embodiments, the message signal will also include data which identifies the status of all digital inputs to the apparatus as well as other information as defined in detail following.

Methods for Monitoring

In general, a method for monitoring water treatment system includes generating a first signal which represents the volumetric rate at which water flows through a treatment system. A second signal is generated and represents a physical characteristic of the water flowing through the treatment system. By integrating the first signal over time, the volume of water which has flowed through the system since a defined event is computed. A call is initiated to a CCS if (a) the total computed volume of water becomes equal to a predetermined volume of water; (b) the actual physical characteristic represented by the second signal becomes equal to a predetermined physical characteristic and the first signal and the second signal coexist, or (c) in a recirculating system, the actual physical characteristic represented by the second signal becomes equal to a predetermined physical characteristic.

More particularly, treatment tanks such as those contained in exchange resin beds have the capability of treating a quantity of water to have a particular physical characteristic. Given the physical characteristic of the water prior to treatment, one of ordinary skill can predetermine within rather narrow limits the total volume of water which fresh tanks are capable of treating. Therefore, the generation of the first signal will have great predictive value in anticipating when the treatment tanks for a particular customer will again need to be changed. This first signal will also have value in detecting changing patterns of customer water usage as well as in detecting changes in input water quality and, possibly, changes in the quality of the treating tanks. In a preferred method, a call will be initiated to a CCS, for example, if the total volume of water represented by the first signal becomes equal to a predetermined volume of water. The predetermined volume of water, represented by signals stored in the interval volumetric register, is selected to be of somewhat less than the total estimated volume of water which may be acceptably treated by the tanks. This approach is preferred since it permits rational scheduling of service vehicles and personnel for tank replacement purposes rather than continually responding to crisis calls.

The second signal may be derived from appropriate instrumentation designed to measure the particular physical characteristic in question. Water temperature, radioactivity, pH and conductivity are examples of some of the kinds of physical characteristics which might be monitored.

At least in the case of a second signal involving water conductivity measurements, it is known that water which is permitted to be quiescent within the treatment system for any significant period of time becomes stagnated. Its conductivity may rise to an apparently unacceptable level, even though the resin beds are well capable of providing water treated to have an acceptable physical characteristic. This type of false reading may be avoided by assuring that conductivity measurements are taken only when water is actually flowing through the treatment system; that is, when the first signal and the second signal coexist.

Therefore, in the preferred method and for a non-recirculating system, a call will also be made if the actual physical characteristic represented by the second signal becomes equal to a predetermined physical characteristic and water is then flowing through the treatment system, as evidenced by the presence of the first signal.

Upon occasion, aberrational measurements of the water physical characteristic may be encountered. This is so, notwithstanding that the treatment tanks are in a state to satisfactorily treat the water and water is flowing through the system, i.e., has not stagnated. To help avoid the initiation of calls in such a circumstance, another highly preferred method will delay initiation of the call for a predetermined time. During this time delay, the actual physical characteristic must be continuously detected to be at least equal to the predetermined physical characteristic and the water must have flowed continuously through the treatment system.

Another preferred method includes generating a third signal which represents or may be used to compute the actual elapsed time measured from the occurrence of a defined event such as the replacement of treatment tanks. Using this third signal and in addition to initiation of calls under conditions as described above, a call may be initiated if the actual interval of time which has elapsed from the time of the defined event becomes equal to a predetermined interval of time. This approach is particularly useful where the treatment system is subject to a usage rate which is highly repetitive over time.

DETAILED DESCRIPTION OF THE PREFERRED EMBODIMENTS

Figure 1:
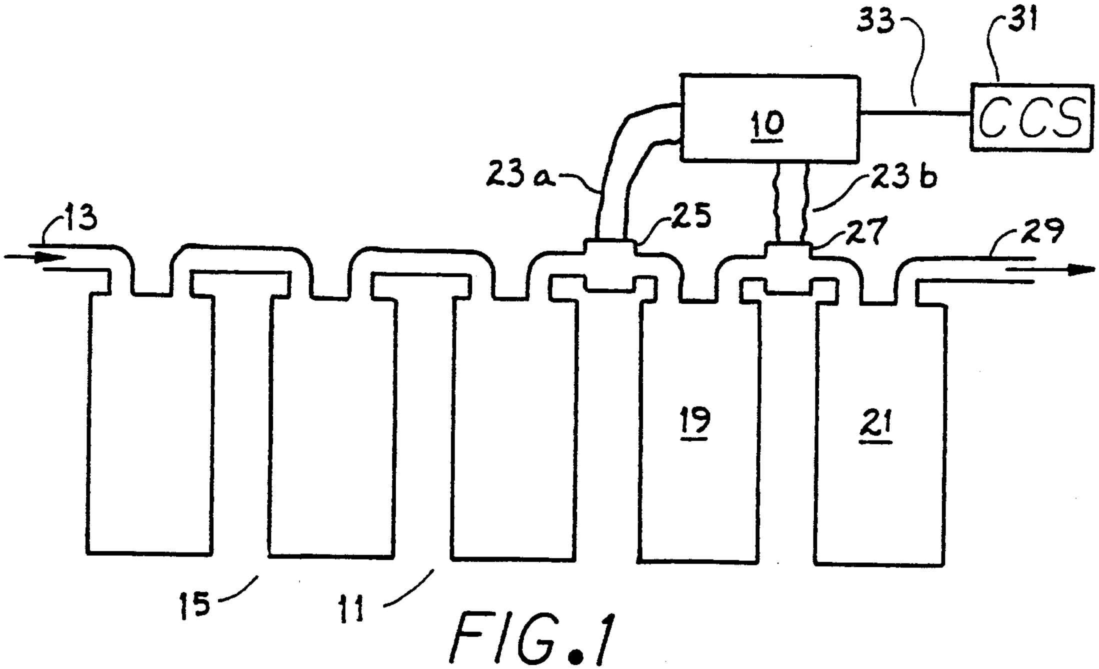
FIG. 1 is a simplified pictorial view of the inventive apparatus shown in conjunction with a water treatment system and a central computer system.

Referring first to FIG. 1, the apparatus 10 is shown in conjunction with a water treatment system 11 which, for purposes of example, is a portable exchange deionizing system. The exemplary system 11 includes an inlet pipe 13 for providing a source of untreated water or of recirculated water which flows through a plurality of ion exchange tanks 15 in series. The system 11 may include one or more particle removal tanks 19 for filtering out solids and a polisher tank 21 for final ion exchange, all in a known configuration. Two of the digital input terminals 23*a*, 23*b* of the apparatus 10 are connected to a conductivity instrument 25 and a flow turbine 27, respectively. A preferred flow turbine 27 for flow rates of 0.25 g.p.m. to 30 g.p.m. will be a 1" turbine, Part No. 481C10G1, while a preferred turbine for flow rates in the range of 2 g.p.m. to 250 g.p.m. will be a 2" turbine, Part No. 480B78G1, both as manufactured by Autotrol Corporation of Milwaukee, Wis. The interface between the apparatus 10 and the turbine 27 is preferably a Sprague Model UGN-3040T/U Hall effect digital switch. The actual configuration of a system may vary from that depicted in FIG. 1. Such variations may occur from site to site and/or the precise locations of the instrument 25 and the turbine 27 may vary from site to site.

The tanks 15, 19, 21, the conductivity instrument 25 and the flow turbine 27 are connected in series with one another as shown and the output pipe 29 is connected to the process for which the treated water is being provided. The apparatus 10 is connected to a central computer system (CCS) 31 by a dedicated or non-dedicated telephone line 33 used to carry message signals from the apparatus 10 to the CCS 31. The line 33 may also be used to download signals from the CCS 31 to the apparatus 10 in a manner which is described in detail following.

Figure 2:
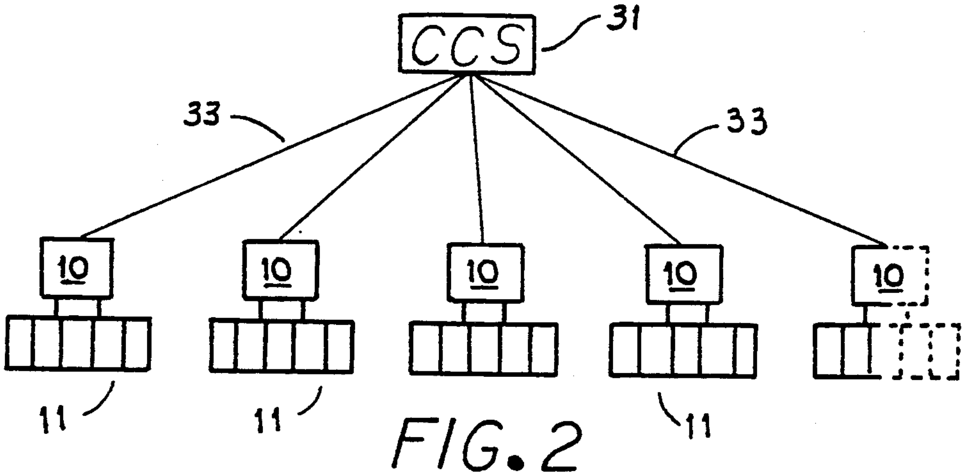
FIG. 2 is a simplified schematic diagram showing several inventive apparatus, each connected to a central computer system and to a water treatment system to be monitored.

Referring next to FIG. 2, several apparatus 10 are shown, each in conjunction with a symbolic water treatment system 11 being monitored by its associated apparatus 10. Each apparatus 10 is connected by a telephone line 33 to the CCS 31 for effecting digital communication. It will not be uncommon for a network as shown in FIG. 2 to include 40–50 apparatus 10 and systems 11, each combination thereof being located at a different site. The advent of the apparatus 10 facilitates that which was heretofore impossible, namely, monitoring of each such combination to permit rational scheduling of tank replacement or other servicing for a very large number of such installations.

Figure 3A:
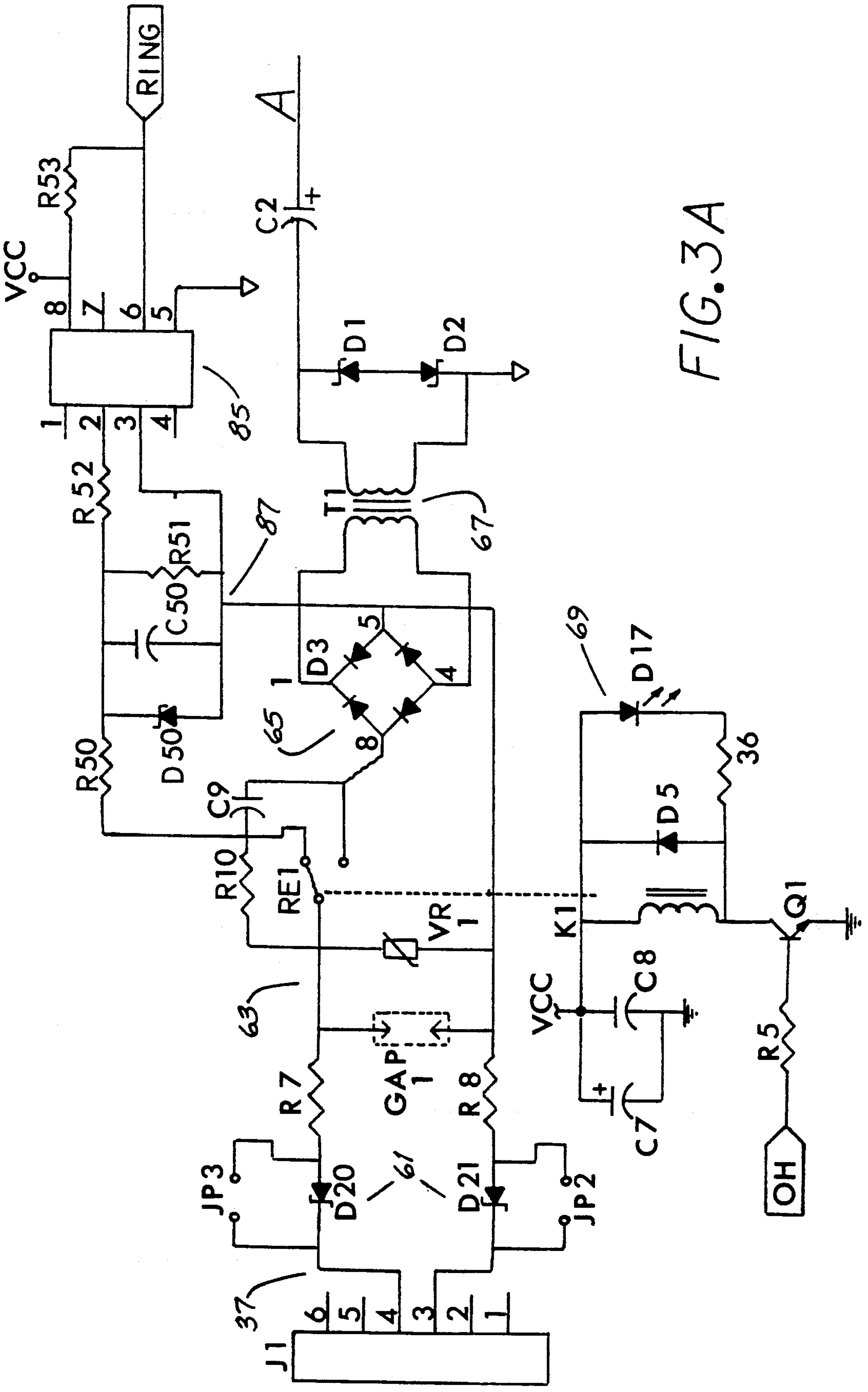
FIGS. 3A through 3N inclusive, taken together, show the electrical schematic diagram for the inventive apparatus.
Figure 3B:
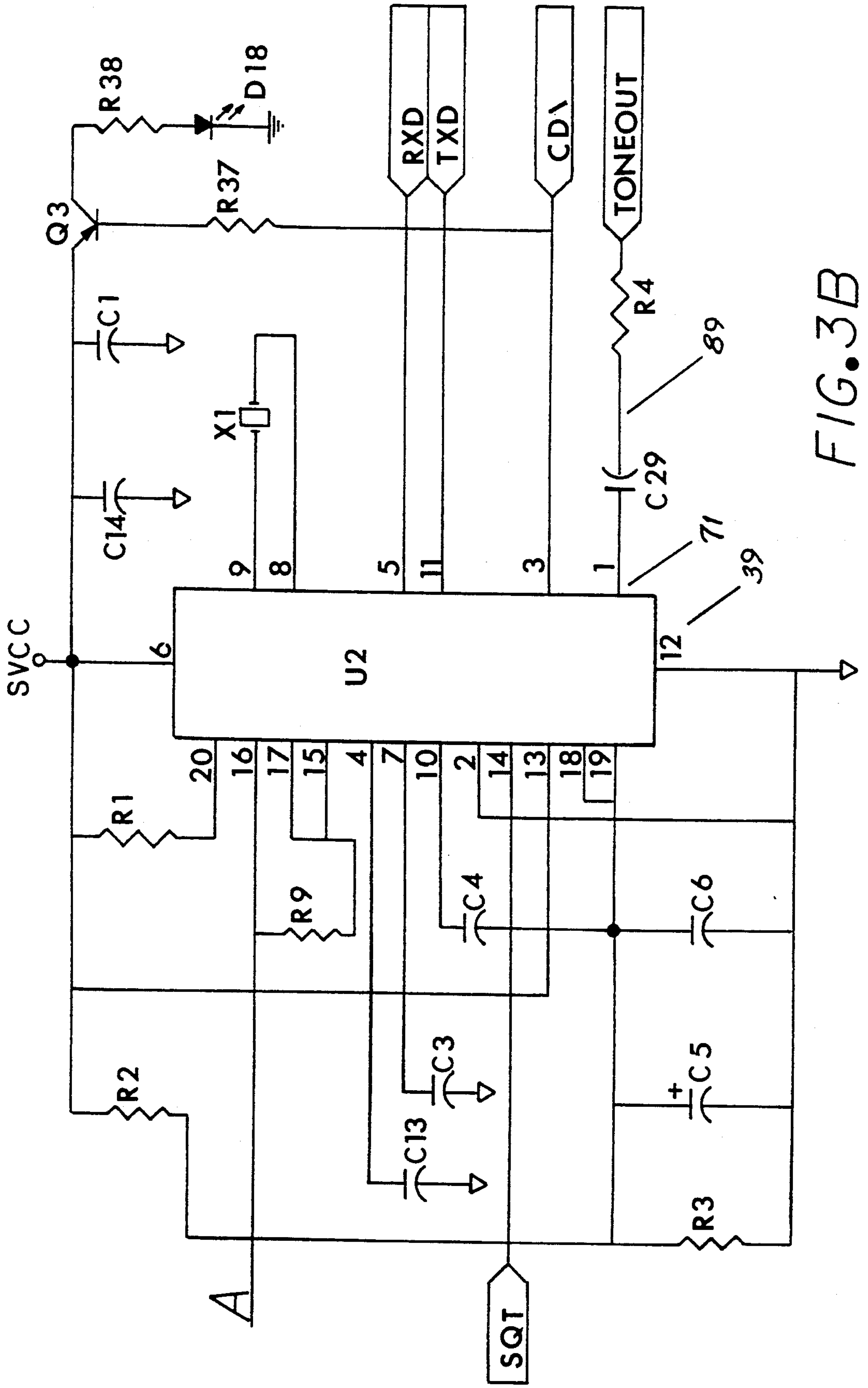
Figure 3C:
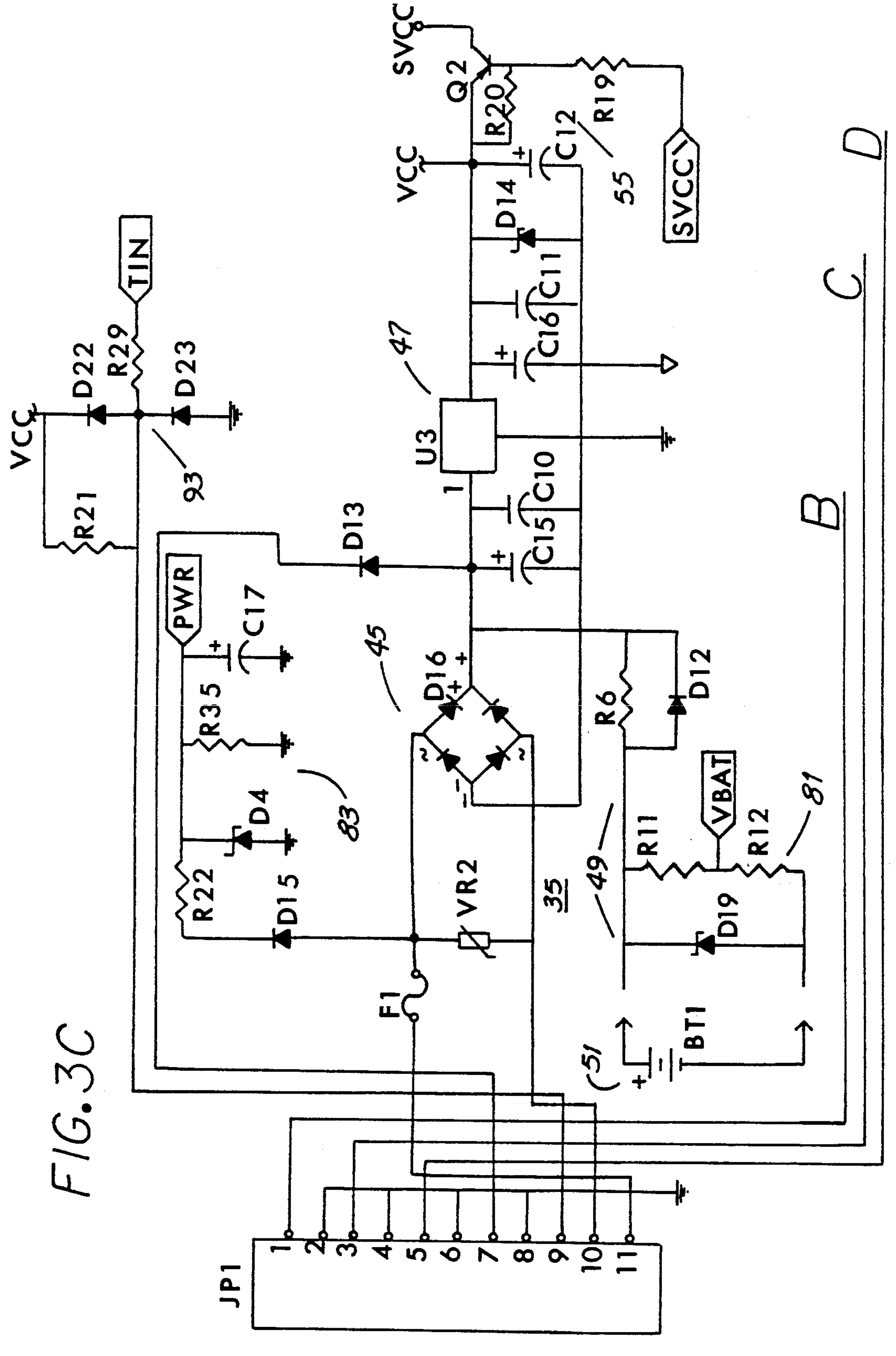
Figure 3D:
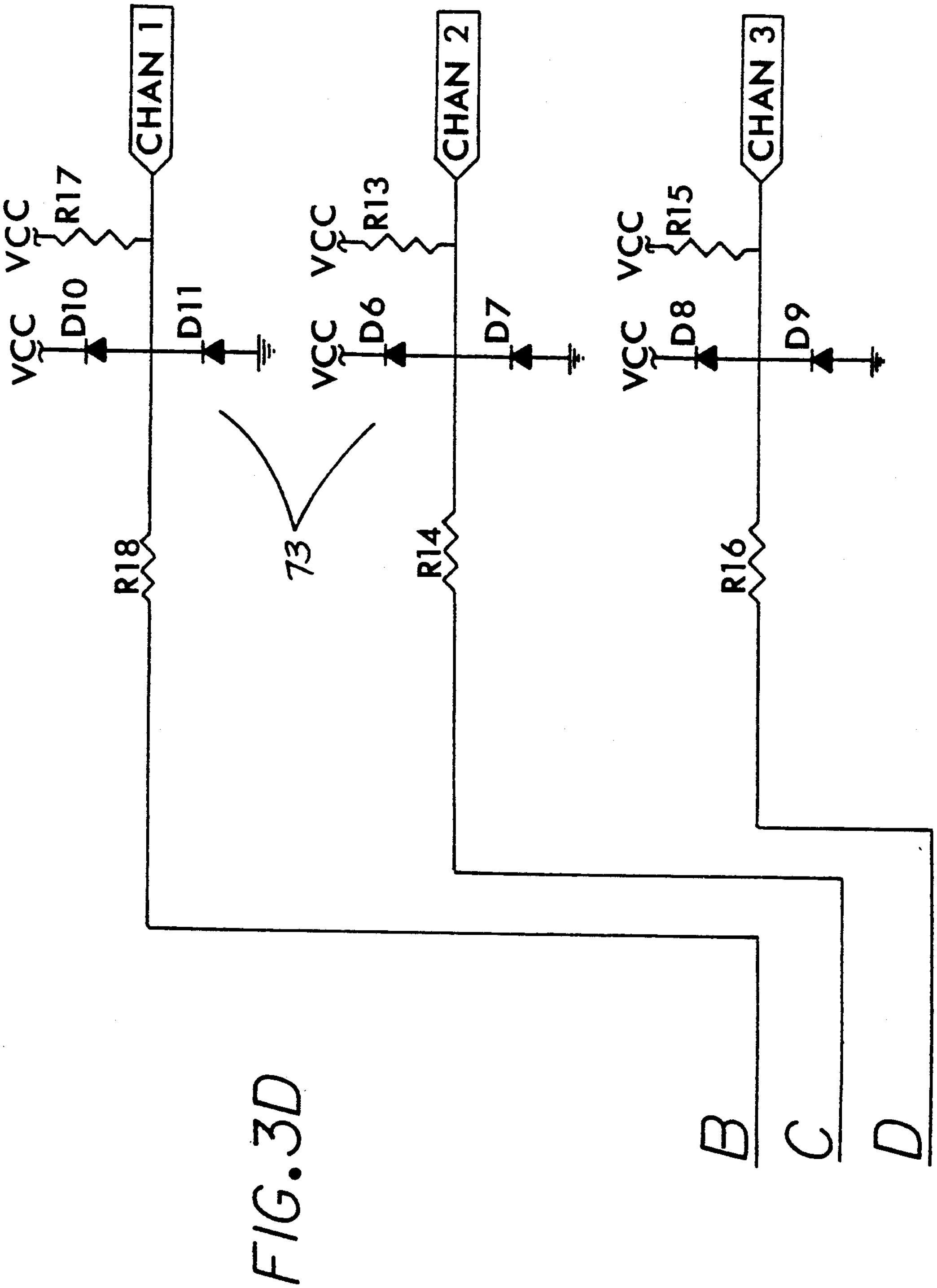
Figure 3E:
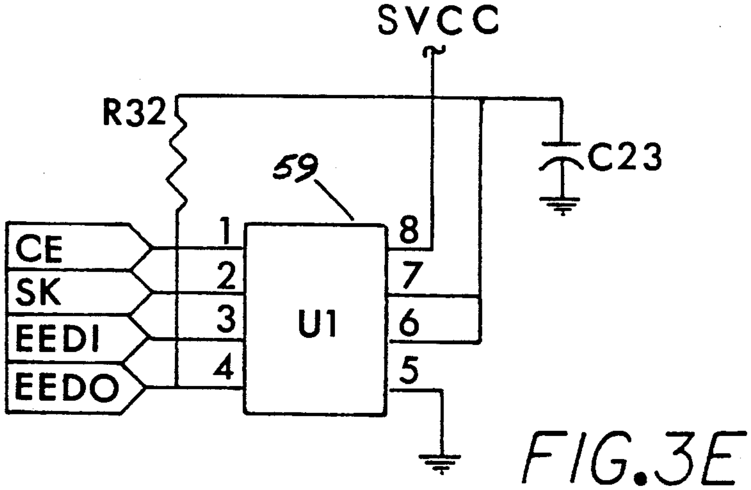
Figure 3F:
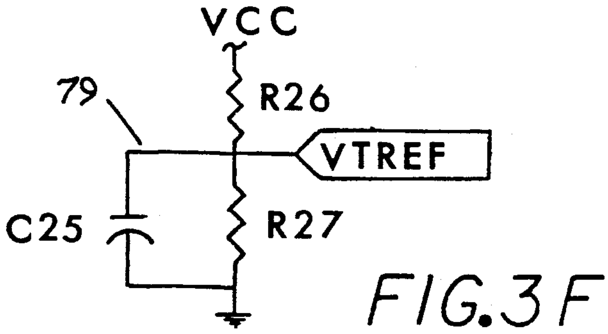
Figure 3G:
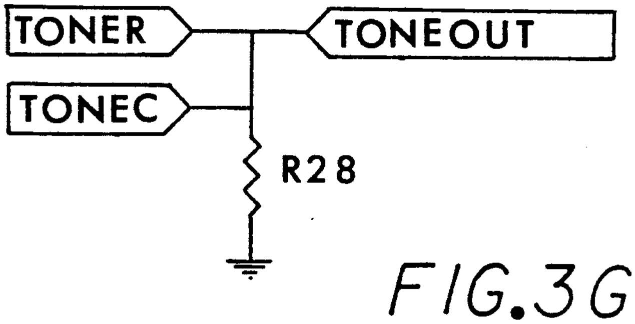
Figure 3M:
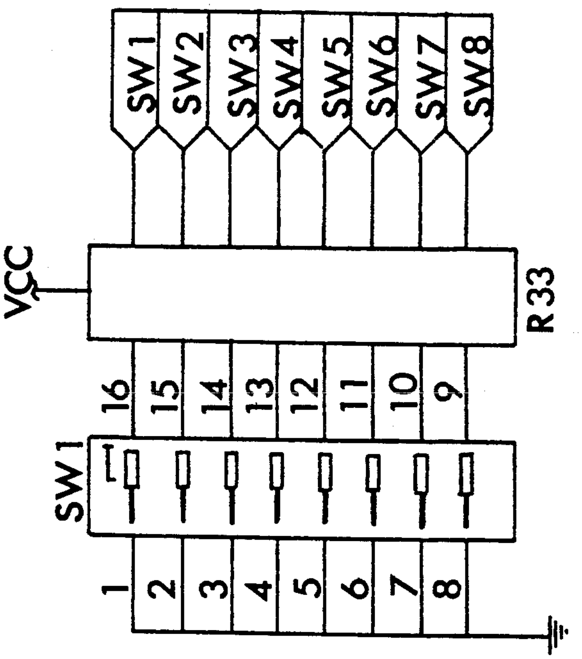
Figure 3H:
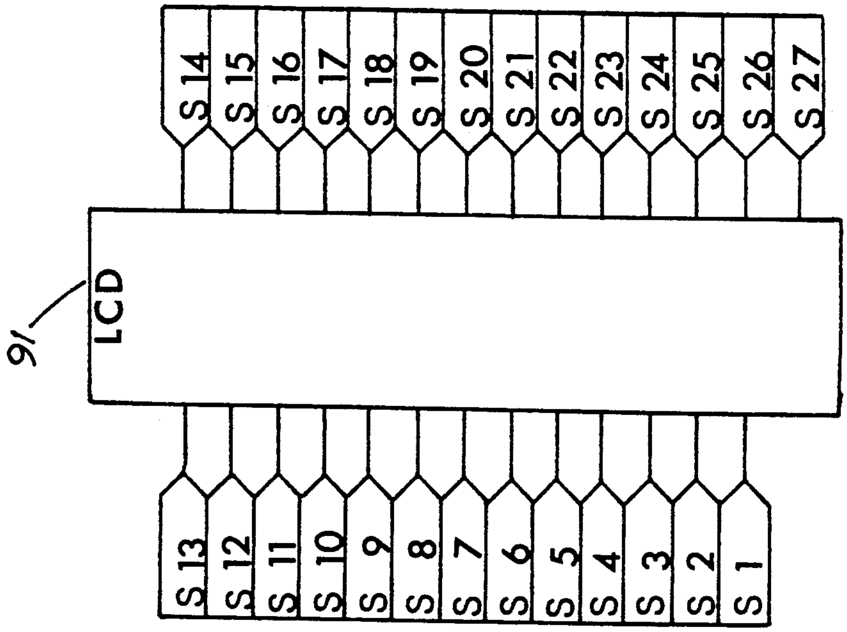
Figure 3I:
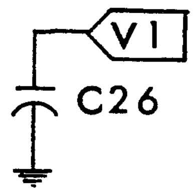
Figure 3J:
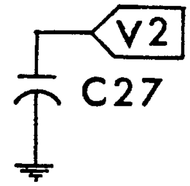
Figure 3K:
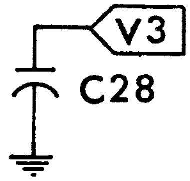
Figure 3L:
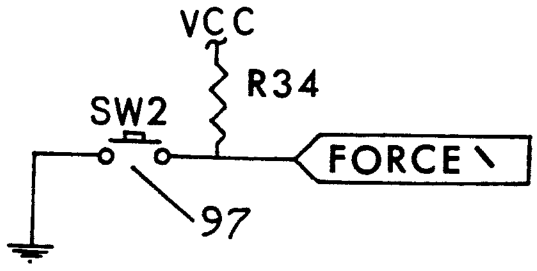
Figures 1, 3N:
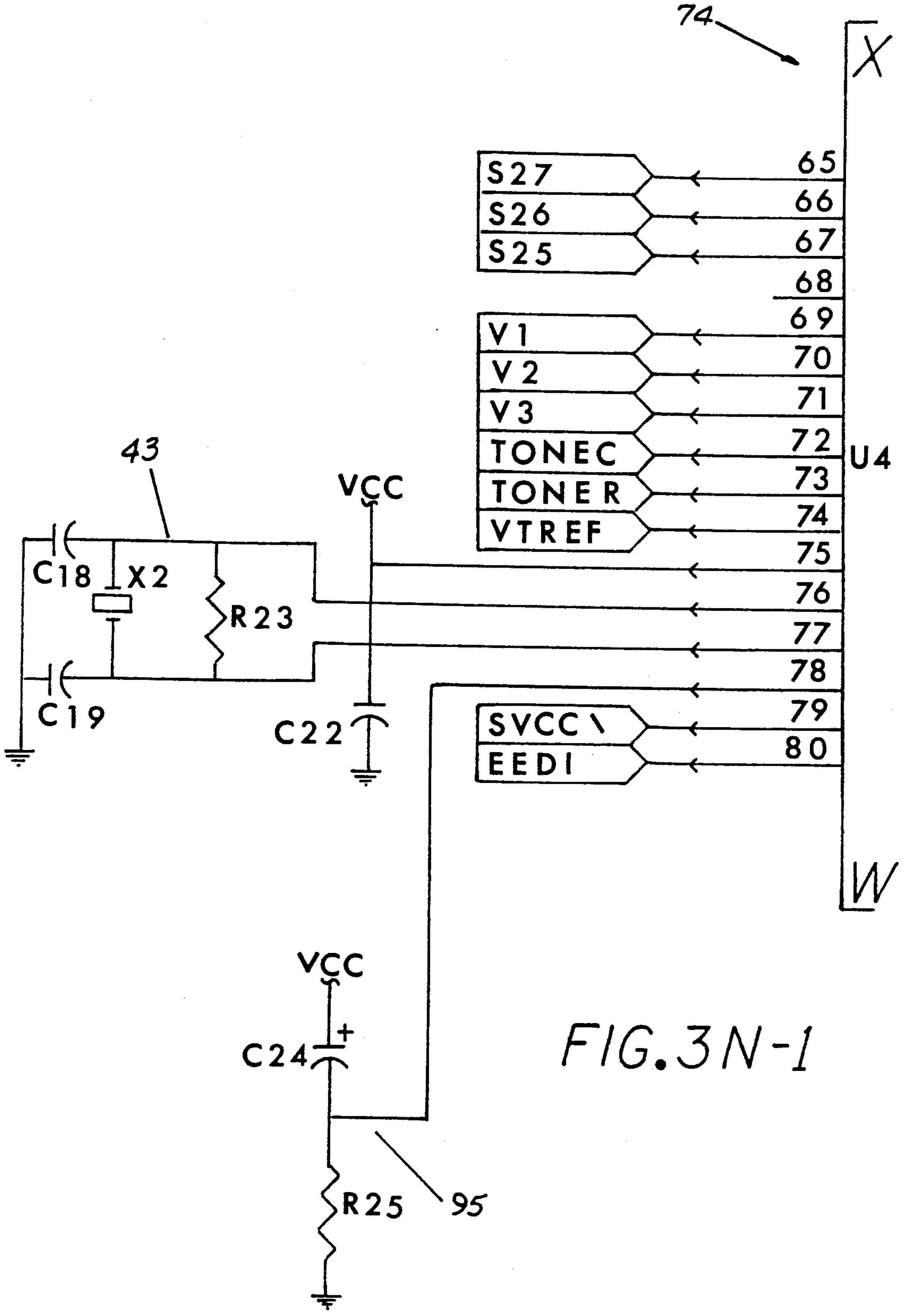
Figures 3, 3N:
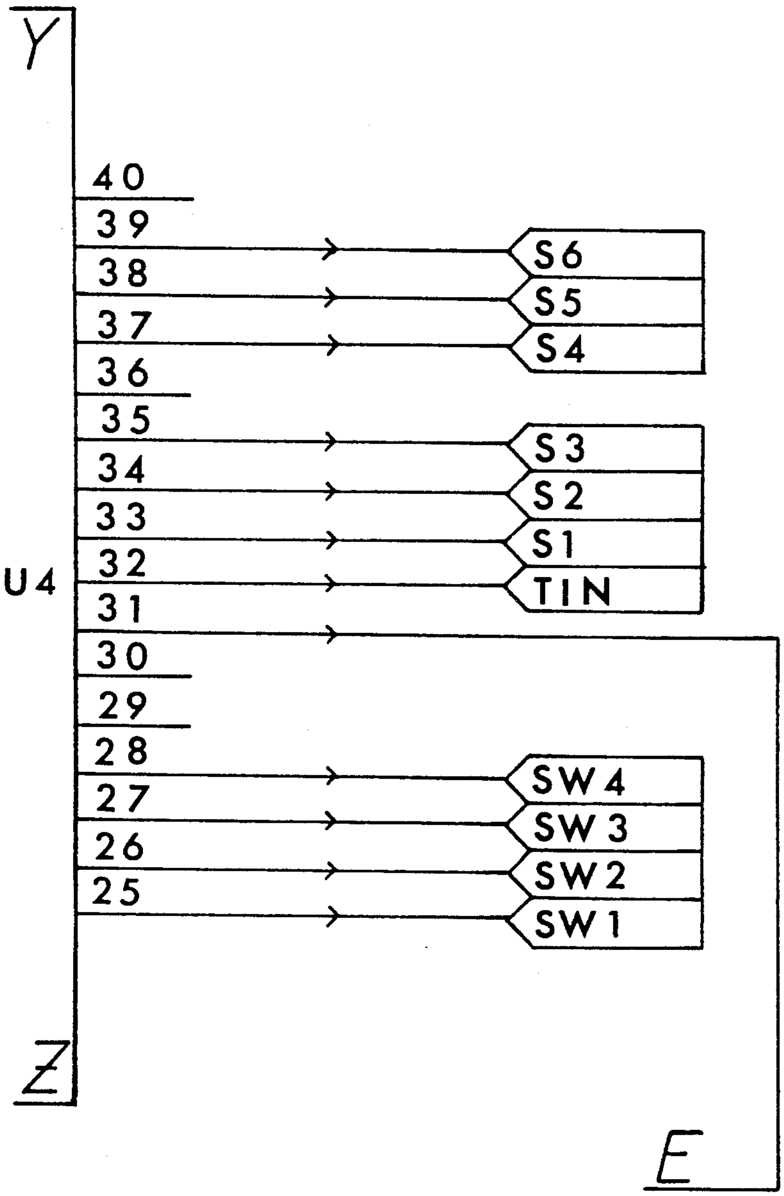
Figures 2, 3N:
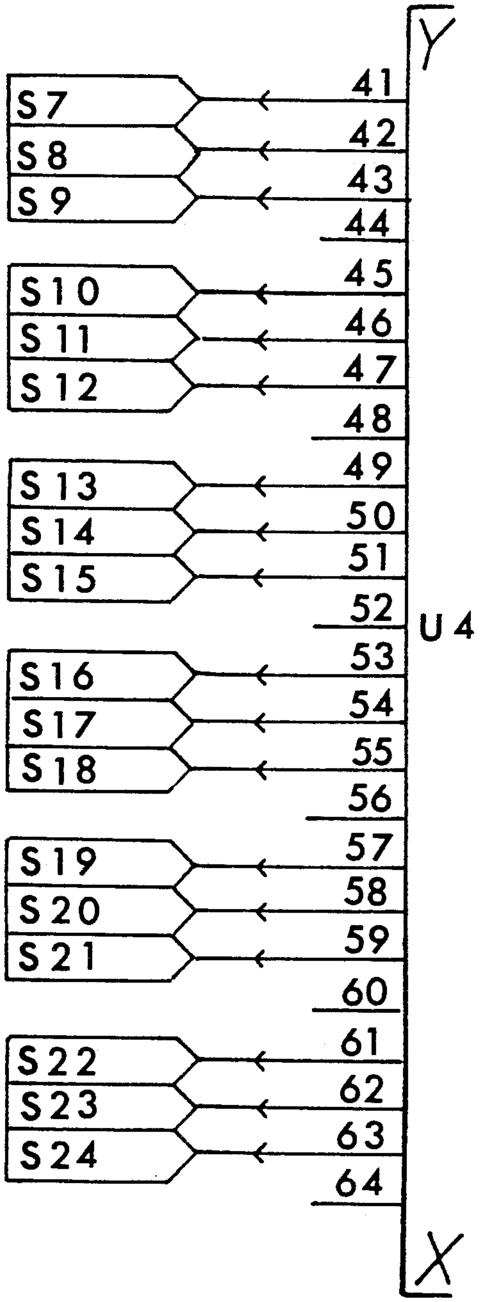
Figures 3, 3N, 4:
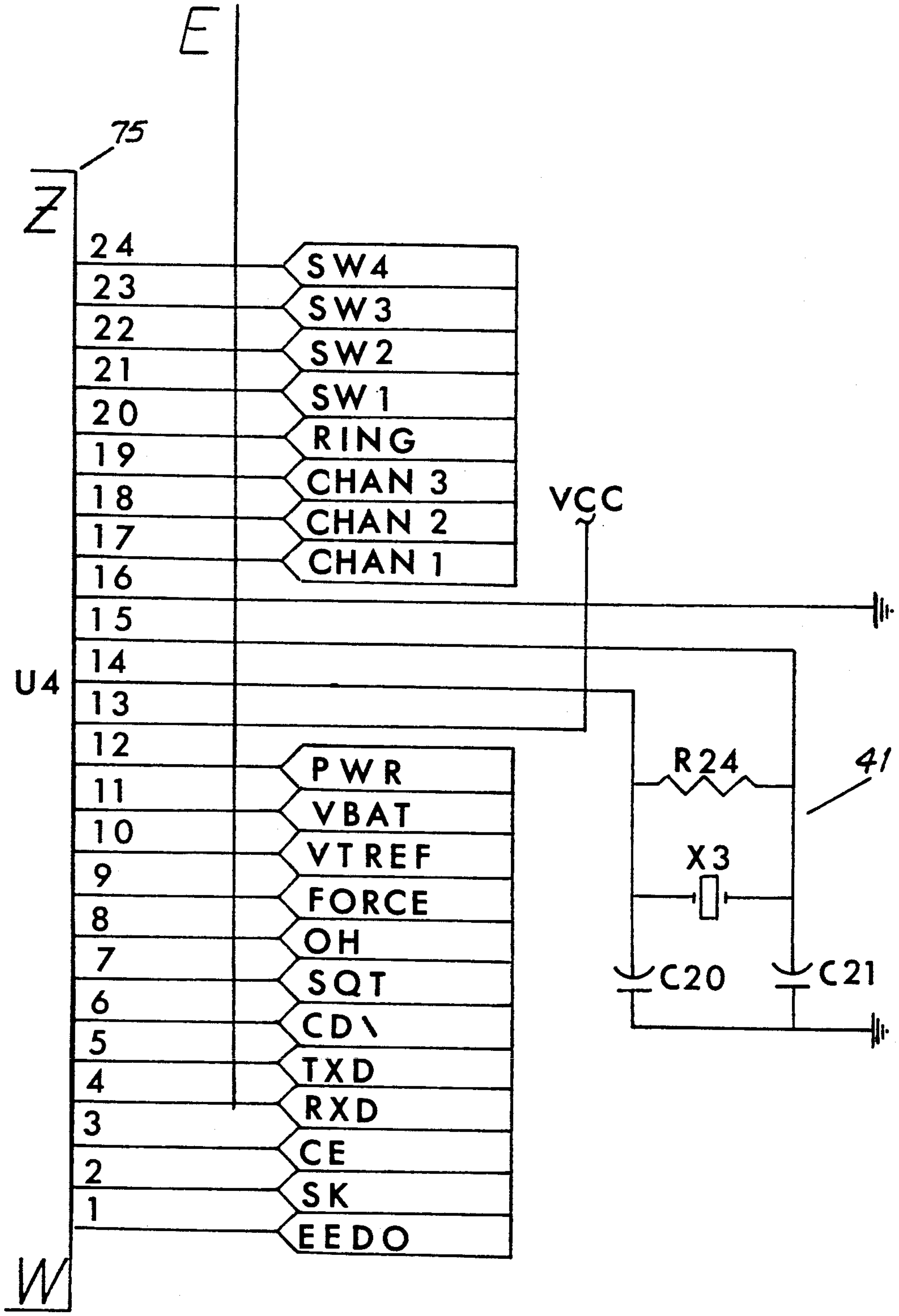

Referring next to FIGS. 3A–3N inclusive, the apparatus 10 is shown to include, as its primary constituents, a power supply 35, a phone line interface 37, a modem 39, a plurality of digital input terminals JP1—1, 3, 5, 9 a clock timer 41 and a processor oscillator 43. The power supply 35 is shown to include pins JP1–10, 11 for receiving 9v. AC input power. This power is rectified by a full wave bridge 45 to an unregulated DC voltage which is directed to a regulating circuit 47, the output of which is 5v. DC. A voltage limiter circuit 49 is provided for charging the battery 51. If no AC power is being provided to the pins JP1–10, 11, unregulated DC power flows from the battery 51 through the forward biased diode D12 to the regulating circuit 47. The diode D13 provides unregulated DC power to the Hall effect switch of a turbine 27 which is connected to the power supply 35 at pin JP1-7. A switching circuit 55 is provided to remove power from the modem 39 and the EEPROM 59 in the event of a failure of AC power.

A phone line interface 37 is provided to connect the apparatus 10 to a telephone line 33 for establishing communication with the CCS 31. The interface 37 includes optional circuitry 61 for preventing interference with an extension phone which may be connected to the same telephone line 33. The interface 37 also includes a circuit 63 for providing protection against phone line transient noise and a bridge 65 to provide proper polarity in the event the phone line is reverse connected. A transformer 67 provides isolation and DC load resistance required to meet the requirements of Federal Communication Commission, Part 68. A diode 69 provides a visual indication of an off-hook condition.

The modem 39 functions as a BELL 103 originate modem for transmitting data through dial-up telephone lines. Provision is made at the pin 71 for coupling the dual tone multi-frequency (DTMF) signal to the modem 39.

A plurality of nondedicated digital input terminals is provided, three in the illustrated embodiment, at pins JP1—1, 3, 5 and their associated grounding pins. Each pin JP1—1, 3, 5 is coupled into a protection network 73 to prevent accidental over-voltages from damaging the microprocessor 75.

A clock timer 41 is provided for generating a plurality of time signals spaced by one second each and used by the microprocessor 75. It uses a resonant oscillator with a frequency of 32.768 kHz which is digitally divided by the microprocessor 75 to produce a one second interrupt signal.

A main processor oscillator circuit 43 generates the main processor clocking signal used for timing all processor instruction execution and to generate the proper frequency for the DTMF signal generator 79. It employs a resonant oscillator with a frequency of 400 kHz for the purpose.

Other subsidiary constituents of the apparatus 10 include a low battery detection circuit 81 for detection by the microprocessor 75 of a battery voltage less than 6.1 volts. A power fail detection circuit 83 provides a signal to the microprocessor 75 whenever AC power is present at the pins JP1-10, 11. A ring detection circuit 85 is provided for generating a signal to the microprocessor 75 that ringing is occurring on the phone line 33 and includes a filtering network 87 for receiving the phone line signal.

A DTMF signal generator circuit 79 provides dialing tones used to connect to a switched phone network. The tones are generated at the microprocessor pins connected to TONEC and TONER and are signalled to the modem 39 through a filter 89. An 8 digit liquid display panel 91 provides a visual indication of signals occurring within the apparatus 10. An EEPROM circuit 59 is provided for storing data such as telephone numbers, look-up tables indicative of the characteristics of the turbine 27, time delay presets, call enable time flags and like. Data is transmitted in a bit serial fashion. The electrical signal generated by the turbine 27 is directed to pin JP1-8 through a protection network 93 which helps prevent accidental overvoltages from damaging the microprocessor 75.

A reset circuit 95 provides a power-on reset signal to the microprocessor 75 each time that AC power is applied to the apparatus 10. A manually operated force switch 97 is provided for initiating a call from the apparatus 10 to CCS 31. Typically, this force switch 97 will be used by service personnel to signal the replacement or other servicing of water treatment tanks.

In a preferred embodiment, the apparatus 10 will include terminals JP1—1, 3, 5, 9 for four binary input signals. Each signal will be defined in the microprocessor 75 as being of the alarm, event or counter type. Identification of the signal type is preferred since it will affect how the CCS 31 manages the resulting data. Of these four input terminals, one of them, pin JP1-9, is dedicated to the reception of signals initiated by the flow turbine 27 and relating to the computation of the volume of water which flows through and is treated by the system 11. In a preferred embodiment, the characteristic curve of the turbine output pulse rate vs. instantaneous flow rate is embedded in the microprocessor 75 as multiple straight line approximations of a 6th order polynomial equation. This will permit characterization of the actual flow rate within a preferred accuracy of about + or −3%.

The three remaining input terminals, pins JP1—1, 3, 5, are arranged to detect a change of state of a dry contact. Characteristics of each of the input terminals, pins JP1—1, 3, 5, may be individually configured in accordance with certain variables including call enable, call delay, link and input type. With respect to call enable, the input terminals, pins JP1—1, 3, 5, may be characterized to specify whether the apparatus 10 will initiate a call to the CCS 31 upon detection of a contact change of state only for that terminal or in combination with changes of state of one or more additional terminals. Any one of the input terminals JP1—1, 3, 5 may also be characterized to be used to reset the interval volumetric register.

In a preferred embodiment, at least the fact of the change of state will be reported on the next initiated call and will continue to be reported with each succeeding call until the contact returns to its normal state. From the foregoing it is to be understood that terminal 23*b* of FIG. 1 is coincident with pin JP1-9 and that terminal 23*a* may be coincident with pin JP1—1, 3 or 5.

For call delay, an amount of time between a contact change of state and the initiation of a call may be selected. In a preferred embodiment, the range of available delay times is 0–999 minutes. The implication of this delay is that the contact change of state must persist during the duration of the specified delay in order for the change of state to be reported to the CCS 31 by a message signal.

Another variable which may be selected for an input terminal JP1—1, 3, 5 will permit the terminal to be linked in AND fashion to another defined condition such as water flow or the state of another input terminal. The conductivity instrument 25 may experience a change of state because that physical characteristic of the treated water has deteriorated to the threshold acceptable value. Nevertheless the input terminal to which the conductivity instrument is connected, JP1—1, 3, 5, may be prevented from initiating a call to the CCS 31 if in a non-recirculating system, there does not coincidently exist a contact state at the flow input terminal JP1-9 which indicates that water flow is occurring. With the call delay feature, the coexistence of a contact state indicating water flow and a change of state of the contacts of the conductivity instrument 25 will not initiate a call unless and until a predetermined time has elapsed. During this time and in a non-recirculating system, the foregoing conditions must continuously persist before a call will be initiated. This feature helps eliminate nuisance calls.

In addition to the foregoing, a preferred apparatus 10 will also permit the selection of that binary contact state, normally open or normally closed, which will be considered as the fault condition.

In a preferred embodiment, the apparatus 10 and the CCS 31 to which it may be connected will use password architecture to permit modification of parameters only by authorized persons. In a highly preferred embodiment, the apparatus 10 is arranged to permit its identification to a particular installation number and a particular telephone number, both by persons who perform field service work. Other parameters may be password accessed in hierarchical fashion by persons of increasing technical capability.

Call Initiation

In a highly preferred embodiment, the apparatus 10 will be arranged to initiate an advisory call to the CCS 31 upon the occurrence of any one of four events. The first such event is the lapse of time. In this instance, the apparatus 10 will initiate a call at the end of each time period selected, every fifteen minutes, every two hours or the like. The periodicity is preferably selected in view of other system parameters. For example, the predictive value of the apparatus 10 may be beneficially employed by observing periodic volumetric usage rates and by comparing those rates with the total treatment capability of fresh tanks. Such time based calls are also useful for detecting changing usage patterns which may necessitate the creation of different tank replacement scheduling routines.

A call may also be initiated upon the occurrence of a fault. Examples of such faults are power failures which persist for some predetermined duration and the detection of water physical characteristics which have deteriorated to an acceptable level. Another example of a fault condition includes a change of state of one of the sensors connected to one of the digital input terminals JP1—1, 3, 5 and such change of state may or may not be accompanied by an AND requirement such as a time delay or a link to another input.

The registry of a predetermined volume of treated water which is passed through the system 11 may also be used to initiate a call. A particularly useful way in which this feature may be used is to establish within the apparatus 10 that predetermined volume of water which can be treated to an acceptable physical characteristic by tanks 15 which have been freshly exchanged or recharged. Thereafter, the flow turbine pulse string is used to generate a first signal. This signal is used by the microprocessor 75 to form a representation of the total volume of water which has passed through the treatment system 11 subsequent to the refurbishment of the tanks 15. When this total becomes equal to the predetermined volume of water, the call may be initiated. In a preferred embodiment, the predetermined volume will be established slightly below the actual treatment capability of the tanks 15 to permit efficient scheduling of servicing personnel.

From the foregoing, it is to be appreciated that the apparatus 10 will periodically send a message signal to the CCS 31 which routinely reports total water usage since the last tank refurbishment and water usage which has occurred since the transmission of the last message signal. This information may be used by the servicing organization to plan highly efficient service routes. However, if the servicing organization should inadvertently fail or be unable to refurbish treatment tanks 15 in accordance with a route plan, the apparatus 10 will initiate an alarm signal when the total volume of water represented by the first signal becomes equal to the predetermined volume of water.

A call may also be initiated manually by actuating the force switch 97. This feature is most frequently used at the time the servicing organization refurbishes the treatment tanks 15. When a manual or forced call is initiated by the servicing representative, the apparatus 10 will cause computer storage of the volume of water treated since the immediately preceding tank replacement This creates a historical pattern of usage and also provides a service record for each customer. The initiation of a manual call will also cause the interval volumetric register to be returned to zero. However, in a preferred embodiment, the total volumetric register will not be reset. These registers are respectively used for the recordation of the volume of treated water since the last time-based status call and since the last tank exchange.

While the configuration of a highly preferred embodiment of the apparatus 10 has been described above, the inclusion of only certain characteristics will nevertheless result in an apparatus 10 which is useful, although not optimally so. Such an apparatus 10 would include a first input terminal, JP1–9 for example, for receiving a first signal representative of a flow rate and a second input terminal, JP1–3 for example, for receiving a second signal representing a physical characteristic. A mircoprocessor 75 has a clock timer 41 and is programmable for receiving and totalizing the first signal to a flow volume. A power supply 35 provides electrical power. The apparatus 10 would initiate an advisory call to a CCS 31 upon the occurrence of either a first condition or a second condition. The first condition would include the registry in the microprocessor 75 of first signals representing a total flow volume equal to a predetermined volume. The second condition would include the coexistence of the first signal (indicating that water is flowing at a flow rate which assures that stagnation has not occurred) and the second signal indicating the threshold physical characteristic at which water quality is unacceptable.

Call Initiation Sequence

When a call is initiated for any one of the foregoing reasons, the apparatus dialer will sample the telephone line 33 to determine its current status, whether in use or available. If it is available, the apparatus 10 will dial the telephone number which has been prior programmed. Upon receiving an answering signal and after performing any handshaking function, the apparatus 10 will transmit a message signal to the CCS 31. Following termination of the data string which represents the message signal, the apparatus 10 will accept new instructions or parameters which may have been placed in the CCS 31 by the operator. Following the downloading of any such new instructions, the call will be terminated.

In a highly preferred embodiment, the data string which makes up each message signal transmitted to the CCS 31 will include several informational components. These components include the program version identifier, the apparatus identifier, total volume of treated water since the last tank replacement and total volume of treated water since the last reporting call. The data string will also include signals representing the status of the contact connected to each input terminal JP1–1, 3,

5 and whether or not the apparatus 10 has experienced power failure. Additionally, the data string will include components indicating the time and date of the call and whether the call was manually initiated.

In the event the apparatus dialer determines that the telephone line 33 is otherwise in use and therefore unavailable, the call will again be attempted following the lapse of a retry time interval. This will occur repetitively until the call is completed. Other reasons why a call may not be successfully completed include a busy CCS 31 or a transmission interruption. In each of those events the apparatus 10 will likewise attempt the call following the lapse of the retry time interval.

It is to be appreciated that while the exemplary treatment system 11 is used for deionizing water to maintain the physical characteristic of conductivity, the apparatus 10 and the CCS 31 may be readily adapted to monitor other types of treatment systems. For example, a treatment system may be arranged for particulate removal and the conductivity instrument 25 replaced by an optical or other scanner or instrument capable of measuring particulate levels. Another example of how the inventive apparatus 10 and method may be used is to remove radioactive contaminants from water and this could be accomplished by replacing the conductivity instrument 25 with a radiation detector. Because of the cost of a direct radiation detector, a level of radiation may be inferred from a measurement of the level of dissolved solids or "hardness leakage" out of the tanks 15. Since the apparatus 10 is a microprocessor based device, it is also to be appreciated that certain programming changes may be required to be made to support other uses. The following components have been found useful in the construction of the apparatus 10. Resistance is in ohms and capacitance is in microfarads unless otherwise indicated.

| | |
|---|---|
| Q1 | 2N3904 |
| Q2, Q3 | 2N2907 |
| R1 | 5.6K |
| R2, R3, R5, R36, R38, R52 | 2.2K |
| R4, R14, R16, R18, R25, R26, R27, R29 | 10K 1% |
| R6, R10 | 100/.5 WATT |
| R7, R8 | 10/.5 WATT |

-continued

| | |
|---|---|
| R9 | 620 |
| R11 | 174K 1% |
| R12, R35 | 220K 1% |
| R13, R15, R17, R23 | 1M |
| R19, R20, R21, R32, R34, R37 | 4.7K |
| R22, R28 | 100K |
| R24 | 22M |
| R33 | 1M PULLUP |
| R50, R51, R53 | 10K |
| SW1 | 8 POS ROCKER |
| T1 | 600:600 |
| U1 | 93C46 EEPROM |
| U2 | 74HC943 MODEM |
| U3 | LP2950 |
| U4 | HD404608 |
| C2, C7, C17, C24, C50 | 10/16V. |
| C1, C3, C4, C6, C8, C10, C11, C22, C23, C25, C26, C27, C28, C29 | .1/50V. |
| C5, C12, C16 | 100 MFD/25V. |
| C9 | .22 MFD/250V. |
| C13, C14 | 1 MFD/25V. |
| C15 | 2200 MFD/25V. |
| C18, C19 | 220 pF |
| C20 | 6 pF |
| C21 | 22 pF |
| D1, D2 | 1N4624 |
| D3, D16 | VM28 BRIDGE |
| D4 | 1N751 |
| D5, D13, D15 | 1N4005 |
| D6, D7, D8, D9, D10, D11, D22, D23 | 1N485B |
| D12 | 1N5818 |
| D14 | ICTE-5 TRANSORB |
| D17 | LED (RED) |
| D18 | LED (YELLOW) |
| D19 | 6.8V. |
| D20, D21 | 1N4702 15 VOLT |
| D50 | 1N755A |
| GAP1 | GT-BC230L GAS TUBE |
| U50 | 6N138 OPTO-COUPLER |
| VR1 | V250LA4 MOV |
| VR2 | 18V MOV |
| X1 | 3.5795 MHz |
| X2 | CSB400P 400 KHZ CERAMIC RESONATOR |
| X3 | 32.768 KHz |
| RE1 | Electrol RA32041D51 off hook relay |

The following comprises the computer program listing for the apparatus 10:

```
S123ØØØØF1EAE6FCFØEAEØF8FØEAF5E6F1EAF3E7F1EAEEE7FØEAF5E6FØEAF5E6F1EBFFE32E
S123ØØ2ØF4EBFØFFF1EBFØFBFØF1F2F8F1F1F2F8F2F1F2F8F3F1F2F8F4F1F2F8F8F1F2F853
S123ØØ4ØF4EBEØFFE1FAE2FAE2FAFØFØFØF4E6F9FØEØE8E8EØEAE8E2FØEØEØE1EØFAE3EF39
S123ØØ6ØEØE1EØFAE3EFEØE1EØFAE3EFEØE1EØFAE3EFEØE1EØFAE3EFEØE1EØFAECE7EFE386
S121ØØ8ØFØEØF4E4FCE2EAFAE1EØE8E8E1EØE1F4E8E7EAFAFØEØEØEBFDE2EØEBFDE2FB
S123ØØ9EEØEBFDE2EØEBFDE2EØEBFDE2EØEBFDE2EØEBFDE2EØEBFDE2EØEBFDE2EØEBEFE3FB
S123ØØBEEEØEBEFE3EØEBEFE3EØEBEFE3EØEBEFE3EØEBEFE3EØEBEFE3EØEBEFE3EØEBEFE336
S123ØØDEEE8E2EØFØEØEØEØEØEØEØEØEØEØEØEØEØEØEØEØEØEØEØEØEØEØEØEØEØEØEØEØE4
S123ØØFEEEØEØEØEØEØEØEØEØEØEØEØEØEØEØEØEØEØEØEØEØEØEØEØEØEØEØEØEØEØEØEØDE
S123Ø11EEEØEØEØEØEØEØEØEØEØEØEØEØEØEØEØEØEØEØEØEØEØEØEØEØEØEØEØEØEØEØEØBE
S123Ø13EEEØEØEØEØEØEØEØEØEØEØEØEØEØEØEØEØEØEØEØEØEØEØEØEØEØECE2FØEEF1E36C
S123Ø15EE8E6FØEØFEF1F1E5F2F1EAFEF4F1EAFEF3F1EAFEF1F1EAFEF5F1EAFEF9F1EAFE49
S121Ø17EF2F1EAFEF6F1EAFEFAF1EAFEF7F1EAFEF3F1EAFEFBF1F4ECFØEØEEEDF1EØ3E
S121Ø19CEØEBFDE2EØEDF1EØEØEBFDE2FØEØE4ECE8E4F1EEE6FCE5ECE8E4F1EBE6FCCA
S1ØBØ1BAE6ECE8E4F1EEE6FCDD
S123Ø2ØØFØEAF2FCF3EAF9F5F3EAECF9F4EAE5E7F4EAEFE7F5EAE9E9FØEAEEFEFØEAF4E6FF
S123Ø22ØFØEAFBFCF3EAFAFEF3EAEFFEF4EAE4E9F4EAFEE6F5EAF2EAFØEAF3FEFØEAF3E5AC
S123Ø24ØFØEAE3FDF3EAF2FCF3EAE3FCF4EAE4EAF4EAEFE9F5EAFBEBFØEAFBFEFØEAF5E5AB
S123Ø26ØFØEAEBFDF3EAFFFCF3EAFBFCF4EAEFEAF4EAF1EBF5EAE8EDFØEAE3FFFØEAF7E575
S123Ø28ØFØEAF3FDF3EAFØFDF3EAE7FDF4EAE1F9F4EAF3ECF5EAF5EEFØEAEBFFFØEAF9E55C
S123Ø2AØFØEAE6FEF3EAE8FEF3EAF9FDF4EAF9ECF4EAE9EFF5EAE2FØFØEAF3FFFØEAFBE538
S123Ø2CØF1EAE5E2F3EAFBFEF3EAFØFEF4EAFFEFF4EAFAEFF5EAEBF1FØEAFBFFFØEAFDE5F9
S123Ø2EØF1EAEFE2F3EAEFFFF3EAE4FFF4EAEDFØF4EAE8FØF2EAE1E9F1EAE2EØFØEAFFE551
```

S123Ø3ØØF1EAF9E2F4EAE4EØF3EAF8FFF4EAFBFØF4EAF6FØF5EAE9E9F1EAE8EØFØEAE1E62E
S123Ø32ØF1EAE6E3F4EAF8EØF4EAECEØF4EAE1F9F4EAE4F1F5EAF2EAF1EAEEEØFØEAE3E644
S123Ø34ØF1EAF1E3F4EAEBE1F4EAEØE1F4EAE1F9F4EAEAF2F5EAFBEBF1EAF4EØFØEAE5E618
S123Ø36ØF1EAFDE3F4EAE1E2F4EAF6E1F4EAE1F9F4EAE1F9F5EAE8EDF1EAFAEØFØEAE7E6E8
S123Ø38ØFØEAEAFBF4EAF7E2F4EAECE2F4EAE1F9F4EAE1F9F5EAF8EEF1EAEØE1FØEAE9E6CØ
S123Ø3AØFØEAEAFBF4EAEBE3F4EAE2E3F4EAE1F9F4EAE1F9F5EAE2FØF1EAE6E1FØEAF4E6B4
S123Ø3CØFØEAEAFBF4EAE5E4F4EAF6E3F4EAE1F9F4EAE1F9F5EAEBF1F1EAECE1FØEAF4E675
S123Ø3EØFØEAEAFBF4EAE3E6F4EAE9E5F4EAE1F9F4EAE1F9F2EAE1E9F1EAF2E1FØEAF4E66F
S123Ø4ØØF2EAE7F9F2EAE7FDF3EAE7E1F3EAECEBF7EAE3E8F7EAFFEBF7EAFØE9FØEAFDE815
S123Ø42ØF2EAF3F9F2EAF3FDF3EAF3E1F3EAE9ECF7EAEDE8F7EAFDECF7EAFDEAFØEAFDE6BC
S123Ø44ØF2EAE2FAF2EAE2FEF3EAE2E2F3EAF8ECF7EAEDE8F7EAFBECF7EAFAEAFØEAFDE6C2
S123Ø46ØF2EAEFFAF2EAEFFEF3EAEFE2F3EAE8EDF7EAEDE8F7EAF9ECF7EAF7EAFØEAFDE68F
S123Ø48ØF2EAFFFAF2EAFFFEF3EAFFE2F3EAF8EDF7EAEDE8F7EAF7ECF7EAF4EAFØEAFDE634
S123Ø4AØF2EAFØFBF2EAFØFFF3EAFØE3F3EAE5EEF7EAEDE8F7EAF5ECF7EAF1EAFØEAFDE655
S123Ø4CØF2EAF6FBF2EAF6FFF3EAF6E3F3EAEØEFF7EAEDE8F7EAF3ECF7EAEEEAFØEAFDE62C
S123Ø4EØF2EAF8FBF2EAF8FFF3EAF8E3F3EAFØEFF7EAEDE8F7EAF1ECF7EAEBEAFØEAFDE2FB
S123Ø5ØØF2EAE8FCF3EAE8EØF3EAE8E4F3EAEØFØF7EAF9E8F7EAEFECF7EAE8EAFØEAFDE62E
S123Ø52ØF2EAF8FCF3EAF8EØF3EAF8E4F3EAEFFØF7EAEBE9F7EAEDECF7EAE5EAFØEAFDE8E1
S123Ø54ØF2EAE7F9F2EAE7FDF3EAE7E1F3EAECEBF7EAE2EBF7EAEBECF7EAE2EAFØEAFDE6F2
S123Ø56ØF2EAE7F9F2EAE7FDF3EAE7E1F3EAECEBF7EAEEEBF7EAE9ECF7EAFFE9FØEAFDE6AC
S123Ø58ØF2EAE7F9F2EAE7FDF3EAE7E1F3EAECEBF7EAE1EDF7EAE7ECF7EAFCE9FØEAFDE69C
S123Ø5AØF2EAE7F9F2EAE7FDF3EAE7E1F3EAECEBF7EAECEDF7EAE5ECF7EAF9E9FØEAFDE676
S123Ø5CØF2EAE7F9F2EAE7FDF3EAE7E1F3EAECEBF7EAE5EEF7EAE3ECF7EAF6E9FØEAFDE661
S123Ø5EØF2EAE7F9F2EAE7FDF3EAE7E1F3EAECEBF7EAECEEF7EAE1ECF7EAF3E9FØEAFDE63F
S123Ø6ØØF4ECE3E8E8E2F4ECE4E6EØEDEAE7EØEDE9E7FØEBEBF8EØEBF2FBE5F5FØEBF2F869
S123Ø62ØFØEBF4F8E5ECEBE7EØEBFAFBE5F5FØEBFBF8FØEBFDF8E4ECEAE7EØEBFAFBE5F5D9
S121Ø64ØFØEBE4F9FØEBE6F9E5ECEAE7EØEBFAFBE5F5FØEBEDF9FØEBEFF9E6ECEAE7C3
S123Ø65EEØEBFAFBE5F5FØEBF6F9FØEBF8F9E7ECEAE7EØEBFAFBE5F5FØEBFFF9FØEBE1FA81
S123Ø67EE4ECE9E7EØEBF9FBE5F5FØEBE8FAFØEBEAFAE5ECE9E7EØEBF9FBE5F5FØEBF1FAA3
S123Ø69EEFØEBF3FAE6ECE9E7EØEBF9FBE5F5FØEBFAFAFØEBFCFAE7ECE9E7EØEBF9FBE5F559
S123Ø6BEEFØEBE3FBE5ECEBE7FØECF8E7E8E6FØF1F1E5EØEDF8E7FØECE4E6E8E6FØECE3E8B7
S123Ø6DEEAECEØEØF1EØEØEØECEØEØEØEØE9FØFØEBFDFBEØEØEØEØEØEØFØEØEØEØEØEØ55
S123Ø6FEEØEØEØEØEØEØEØEØEØEØEØEØEØEØEØEØEØEØEØEØEØEØEØEØEØEØEØEØEØECE2CA
S121Ø71EFØEBFDFBFØEØE5E9E9E7E8FBE5E9EAE7E8FBE1EDF8E7EAFBE1EBFEFAE8FBDA
S123Ø73CF4ECECE7E2EDF8E7EAFBE1EBFEFAE8FBF4ECEDE7E3EDF8E7EAFBE1EBFEFAE8FBBD
S121Ø75CF4ECEEE7E4EDF8E7EAFBE1EBFEFAE8FBF4ECEFE7EØEDEDE5EØE9ECE7E3FEB8
S123Ø77AEØE9EDE7E3FEE8EDF8E7EAFBE5EDF8E7EAFEFØECEDE5E8E6FCF1F1E5E1EBFEFAAD
S123Ø79AF1EBEØE2F4ECFØE3F1EBF7E1E1EBFEFAF1EBEØE2F4ECF1E3F1EBF7E1E1EBFEFAA8
S123Ø7BAF1EBEØE2F4ECF2E3F1EBF7E1E1EBFEFAF1EBEØE2F4ECF3E3F1EBF7E1E1EBFEFA84
S123Ø7DAF1EBEØE2F4ECF4E3F1EBF7E1E1EBFEFAF1EBEØE2F4ECF5E3F1EBF7E1E1EBFEFA6Ø
S123Ø7FAF1EBEØE2F4ECF6E3F7F9E1EBFEFAEØFAF4ECF7E3F7F9E1EBFEFAEØFAF4ECF8E3F3
S123Ø81AF7F9E1EBFEFAEØFAF4ECF9E3F7F9E1EBFEFAEØFAF4ECFAE3F7F9E1EBFEFAEØFA97
S121Ø83AF4ECFBE3F7F9E1EBFEFAEØFAF4ECFCE3F7F9E1EBFEFAEØFAF4ECFDE3F7F953
S121Ø858E1EBFEFAEØFAF4ECFEE3F7F9E1EBFEFAEØFAF4ECFFE3ECE2E8E2F4ECEDE535
S123Ø876E4E8EDE7F6F1E3FAE1FAFØF1F4ECF6E7FØEBEAFBE1EBFEFAFØEBE8FBF4ECFØE788
S123Ø896E7EDF8E7FØEBEAFBE1EBFEFAFØEBE8FBF4ECF1E7E8EDF8E7FØEBEAFBEDE9EAE778
S123Ø8B6FØEBE8FBECE9E8E7FØEBE8FBE9EDF8E7FØEBEAFBEAE9EAE7FØEBE8FBEØE9E9E799
S123Ø8D6FØEBE8FBEBEDF8E7FØEBEAFBEAE9EAE7FØEBE8FBEØE9E9E7FØEBE8FBEBEDF8E759
S123Ø8F6FØEBEAFBFØEBEAFBE8ECEØEØE6F3ECEBFFEFEECECAE7F1EBEBE4E6F3F1EBEBE455
S121Ø916E8F7ECEØEØEØEØEØEBFBFBEDECEAE7F1EBF7E4E6F3F1EBFAE4E6F7EØEØEØEØ5Ø
S121Ø934ECEBFBFBEEECEAE7F1EBE3E5E6F3F1EBE6E5E6F7EØEØEØEØEØEØEBFBFB33
S123Ø952EFECEAE7F1EBFØE5E6F3F1EBF3E5E6F7EØEØEØEØEØEBFBFBECECE9E7F1EBFCE514
S123Ø972E6F3F1EBFFE5E6F7EØEØEØEØEØEØEBFBFBEDECE8E7F1EBE6E6E6F3F1EBEBE6E6F7F4
S121Ø992EØEØEØEØEØEØEBFBFBEEECE9E7F1EBF5E6E6F3F1EBF8E6E6F7EØEØEØEØF1
S121Ø9BØEØEØEBFBFBEFECE9E7F1EBE1E7E6F3F1EBE4E7E6F7EØEØEØEØEØEBF9FBE6F79C
S123Ø9CEEØEBFBFBEØEBFBFBE4ECEØEØFØEØE1EDEAF3E8ECE2EØF1EØF4ECE5E6EAECE1EØCF
S121Ø9EEE4ECEØEØEØEDEEEØE8EDEFEØFØF2F4ECE3E2ECECE3E2E1EBF6F6EDECE3E2A6
S121ØAØCE1EBE6F8EEECE3E2E1EBF2F9FØECE3E2F4ECE5F3FØECE6E4E1F4F4ECE6E44A
S123ØA2AF1E9E6E4FAF8F1EBF1F6EØEDE4F3FØECE1E7EFF4F4ECE1E7FEF5E5F9EØEDE1E716
S123ØA4AFØECFBE4EFF4F4ECFBE4FEF5F9F9E9EDFBE4FØECFAE4EFF4F4ECFAE4FEF5F9F951
S123ØA6AE9EDFAE4EØEDFBE4FØECFFE4EFF4F4ECFFE4FEF5EDFAE9EDFFE4FØECFEE4EFF476
S121ØA8AF4ECFEE4FEF5EDFAEØEDFEE4EØEDFFE4EØEDE6E4FØECE5E4E1F4F4ECE5E495
S123ØAA8FAE9E5E4E2FBEFECE2E2E2FBF1EBF1F6FØECFCF2E1F4F4ECFCF2F5FBEØE9F1E566
S121ØAC8FCFAEØEDE5E4FØECEBEØF4ECEBF3FØECEAEØF4ECECF3EØEDEAEØEØEDEBEØ87
S121ØAE6EFEDF1E5FØECE4E4E1F4F4ECE4E4F6E9E4E4E2FCEFECE2E2E2FCF1EBF1F656
S123ØBØ4FØECE5E5EFF4F4ECE5E5FEF5FAFDE9EDE5E5FØECE4E5EFF4F4ECE4E5FEF5FAFDF5
S123ØB24E5EDE4E5FØECE3E5EFF4F4ECE3E5FEF5FAFDE9EDE3E5FØECE2E5EFF4F4ECE2E51E
S121ØB44FEF5FAFDE3EDE3E5E2EDE2E5FØECE1E5EFF4F4ECE1E5FEF5FAFDE9EDE1E5C6
S121ØB62FØECEØE5EFF4F4ECEØE5FEF5FAFDE9EDEØE5EØE9E5E5E6FFEØE9E4E5E6FFD4
S123ØB8ØEØE9E3E5E6FFEØE9E2E5E6FFEØE9E1E5E6FFEØE9EØE5E6FFE7ECE1E6FØECE4E93C
S123ØBAØF4ECEØE5FØECE5E9F4ECE1E5FØECE6E9F4ECE2E5FØECE7E9F4ECE3E5FØECE8E3E9

S1230BC0F4ECE4E5F0ECE9E9F4ECE5E5F0ECE3F3EFF4F4ECE3F3FEF5F1EBECF0E9EDE3F36E
S1230BE0F0ECE2F3EFF4F4ECE2F3FEF5F1EBECF0E5EDE2F3F0ECE1F3EFF4F4ECE1F3FEF51C
S1210C00ECF0E9EDE1F3F0ECE0F3EFF4F4ECE0F3FEF5ECF0E9EDE0F3F0ECE9E5EFF4F2
S1210C1EF4ECE8E5FEF5F0F9E5EDE8E5F0ECE8E5EFF4F4ECE8E5FEF5F0F9E5EDE8E5D2
S1230C3CF0ECE7E5EFF4F4ECE7E5FEF5F0F9E9EDE7E5F0ECE6E5EFF4F4ECE6E5FEF5F0F9CE
S1230C5CE9EDE6E5EFE9EAE5E1FAE0E9E9E5E1FAE0E9E8E5E1FAE0E9E7E5E1FAE0E9E6E56A
S1210C7CE1FAE6ECE1E6F0ECF1E6EFF4F4ECF1E6FEF5F5FAE9EDF1E6F0ECF0E6EFF471
S1210C9AF4ECF0E6FEF5F5FAE0EDF0E6E0EDF1E6F0ECF5E6EFF4F4ECF5E6FEF5E9FB2D
S1230CB8E9EDF5E6F0ECF4E6EFF4F4ECF4E6FEF5E9FBE0EDF4E6E0EDF5E6F0ECF9E6EFF450
S1210CD8F4ECF9E6FEF5FDFBE9EDF9E6F0ECF8E6EFF4F4ECF8E6FEF5FDFBE0EDF8E6AA
S1230CF6E0EDF9E6F0ECFEE6EFF4F4ECFEE6FEF5FCFCE9EDFEE6F0ECFDE6EFF4F4ECFDE6ED
S1210D16FEF5FCFCE9EDFDE6F0ECFCE6EFF4F4ECFCE6FEF5FCFCE0EDFCE6E0EDFDE66A
S1210D34E0EDFEE6E0EDE4E4F0ECE3E4E1F4F4ECE3E4FAE9E3E4E7FDF1FEE0EDE3E427
S1230D52F0ECE2E4E1F4F4ECE2E4F6E9E2E4F2FDF1FEE0EDE2E4F0ECE1E4E1F4F4ECE1E42F
S1230D72FAE9E1E4E9FEF4F1E4E8E1E4F1FEF2F1E4E8E0E4F1FEE0EDE1E4E0EDE0E4F1FEF5
S1210D92E0EDE1E4F0ECE0E4E1F4F4ECE0E4F1FEF0ECE5E6EAECE1E0F1E0ECECE5F3E6
S1230DB0F1EBE5F8F0ECE3F2E1F4F4ECE3F2EAE9E3F2F1EBE5F8E0EDE3F2F0ECE2F2E1F4A3
S1210DD0F4ECE2F2EAE9E2F2F1EBE5F8E0EDE2F2F0ECE1F2E1F4F4ECE1F2EAE9E1F26F
S1210DEEF1EBE5F8E0EDE1F2F0ECE0F2E1F4F4ECE0F2EAE9E0F2E5F8E0EDE0F2F0E064
S1230E0CEDECE5F3F1F9F0ECE7F2E1F4F4ECE7F2EAE9E7F2F1F9E0EDE7F2F0ECE6F2E1F41F
S1210E2CF4ECE6F2EAE9E6F2F1F9E0EDE6F2F0ECE5F2E1F4F4ECE5F2EAE9E5F2F1F9DF
S1230E4AE0EDE5F2F0ECE4F2E1F4F4ECE4F2EAE9E4F2F1F9E0EDE4F2F0E0EEECE5F3FDFAF4
S1210E6AF0ECEBF2E1F4F4ECEBF2EAE9EBF2FDFAE0EDEBF2F0ECEAF2E1F4F4ECEAF281
S1210E88EAE9EAF2FDFAE0EDEAF2F0ECE9F2E1F4F4ECE9F2EAE9E9F2FDFAE0EDE9F265
S1230EA6F0ECE8F2E1F4F4ECE8F2EAE9E8F2FDFAE0EDE8F2F0E0F0ECEAE7E3E9E9E7EFFE9E
S1210EC6ECE7EFE3F0E0E4E9E9E7EFFBF7E9EAE7EFFBE9F4ECE7EFE3F0E0E1EBF6FB64
S1210EE4E5EBE6E6F0EBEEE0F7F5E1FCF9F5E1FCE7F4F4ECEAE7E4EDE9E7E0FCF0E038
S1210F02F4ECEAE7E3EDE9E7F0E0E3EDF2E0E8EDF0E1E2EDF1E1E0EDF2E1E3EDF3E181
S1230F20EBEDFBE1E5EDFCE1E3EDFDE1E7EDF3E0E5EDF4E0E9EDE8E0EBECE1E0E0EDEAE081
S1230F40E0EDEBE0E8ECE2E0E9ECE2E0E7EDE9E0E0EDEEE0E0EDEFE0E8EDEDE0E0EDEEE2F7
S1230F60E0E2EFE0E5ECE0E1E0EDEEE0E0EDEFE0ECEDE4E0EBECE0E0E9F3E6F3E5F0E1F375
S1230F80E4F6E6F3E0F7F3E7F0F0EFF1F0F4E8FEEEF1F0F4E9FEEDF1F0F4ECFEECF1F0F44E
S1230FA0EFFEF2E7E4F1F0F4F3FEF0E7E7F1E5EFE8F1E5EFE9F1FAF0E6EFEAF1E5EFEBF188
S1210FC0E5EFECF1E5EFEDF1E5EFEEF1E5EFEFF1E5EFE6EBE0F5E6EBE0F5F0ECE4E97C
S1230FDEF4ECE2E5F0ECE5E9F4ECE1E5F0ECE6E9F4ECE2E5F0ECE7E9F4ECE3E5F0ECE8E9A7
S1230FFEF4ECE4E5F0ECE9E9F4ECE5E5F0ECE0E9F4ECE6E5F0ECE1E9F4ECE7E5F0ECE2E995
S123101EF4ECE8E5F0ECE3E9F4ECE9E5E3EDE0E2E0EDE1E2E6EDFCE4E0EDE8E4E0EDFAE492
S123103EE0EDFBE4EFEDFDE4E0EDF0E5E0EDF1E5E0EDECF3E0EDEBF3E0EDEAF3E0EDE2E04E
S123105EE0EDEBE7E0EDF8E7E0EDEAE5F0ECFBF2E1F4F4ECFBF2FBF9EBECE2E6EBECFFE5CE
S121107EEFECF0E4E9EFE4E8E8F4FAFCF0ECF1E4E9EFE4E8E9F4FAFCF0ECF2E4E9EF78
S121109CE4E8EAF4FAFCF0ECF3E4E9EFE4E8EBF4FAFCF0ECF4E4E9EFE4E8ECF4FAFC38
S12110BAF0ECF5E4E9EFE4E8EDF4FAFCF0ECF6E4E9EFE4E8EEF4FAFCF0ECE5E2E9EF37
S12110D8E4E8E0F4FAFCF0ECE6E2E9EFE4E8E1F4FAFCF0ECE7E2E9EFE4E8E2F4FAFC08
S12110F6F0ECE8E2E9EFE4E8E3F4FAFCF0ECE9E2E9EFE4E8E4F2FAFCF0ECEAE2E9EF2A
S1231114E4E8E5F4FAFCF0ECEBE2E9EFE4E8E6F4FAFCF0ECECE2E9EFE4E8E7F4FAFCE5FDFE
S1231134E7ECE2E6E7ECFFE5E4F1F5F0E0E0E9F1E0E0E2E0E0E0E5F1F0F0FFF4E7FDE6F14D
S1231154FFF4EAFDE0EBEBE2E6EBF6E4E4ECE0E0E5EBE6F3EDECF0EAF8FDE0FEF0ECE3E4F3
S1211174E4E8E7E4F4ECE7E4E7EBECE7F0F2F4ECEDE4E1ECECE9EFFEF1F1FCE8EDE4B1
S1231192F4ECEDE4ECECEDE4F0FEECE7F1FEEFE7F0ECEEE6E0E5F4ECEEE6EDECF4E9FEFE7E
S12311B2F0F1FCE8EDE4F4ECEDE4EDECEDE4E3FFECE7E4FFEFE7F0ECF2E6E0E5F4ECF2E687
S12311D2EDECFCE9F1FFF4F1FCE8EDE4F4ECEDE4EEECEDE4F6FFECE7F7FFEFE7F0ECF6E809
S12311F2E0E5F4ECF6E6EDF5F2EBE1E8EFE7E2F6ECE7F0ECFAE6EDE5F4ECFAE6EAF5EBF84A
S1231212ECE7ECF8EFE7F0ECFFE6E0E5F4ECFFE6ECF5F5F6EFE7F6F6ECE7F0ECE0E7E0E513
S1231232F4ECE0E7E6EBE9FDEFF9E0E9E1E7EAF9F0ECE2E7E1F4F4ECE2E7E2EDE1E7EFF930
S1231252EFF9F0ECE2E7E8E6FAF1F1E5F0F9E0E9E4F3E9FAEFEDE4F3F0ECEFE6E8E6F0F1DD
S1231272F2E5F2ECF3E6E3E6F2F1F2E5F0ECF7E6E8E6F4F1F2E5F0ECFBE6E8E6F6F1F2E5E8
S1211292E0E9FFE6F2FAE9ECFEE5E4ECE1E6E3EFE8E9F0ECE0E8F4E8F0E4F8FAFEFB74
S12312B0F0ECE1E8F4E8F1E4FEFAFEFBF0ECE2E8F4E8F2E4E4FBFEFBF0ECE3E8F4E8F3E449
S12312D0EAFFFEFBF0ECE4E8F4E8F4E4F0FBFEFBF0ECE5E8F4E8F5E4F6FBFEFBF0ECE6E8EA
S12312F0F4E8F6E4FCFBFEFBE8ECE1E6F0ECE0E8E4E8FDE5EFFCF0ECE1E6E4E8FEE5EFFCC4
S1231310F0ECE2E6E4E9FFE5EFFCF2EBF2E5ECECE1E6FAFCECECE2E6FAFCE2EBF9F4FAFCEB
S1231330F2EBF2E5F0ECE0E9F4ECE8E5F0ECE1E9F4ECE7E5F0ECE2E9F4ECE8E5F0ECE3E947
S1231350F4ECE9E5EFEDEAE5E4ECF0E5E0F3E6F7E9F7F1F1E6EBE6EFE5EBE6F3E0EBEBE228
S1211370F2F1E6EBE6EFE5EBE6F3E0EBEBE2F3F1E6EBE6EFE5EBE6F3E0EBEBE2F4F1E1
S123138EE6EBE6EFE5EBE6F3E3EBF1F0E0EDFEE4E4EDFFE4E0E9F4EAF5FEFDFEF0ECF4EA8E
S12313AEF4ECFEE4F0ECF5EAF4ECFEE4F5F1E6EBE6EFE6F7E0EBE9E3E5EBE6F3E0E9FEE487
S12313CEEDFFE0E9FFE4EDFFF2EBE7F1E7F5E3FFF6F1E6EBE6EFE5EBE6F3E8F3E0EBE9E35C
S12313EEEBECE0E0E3EDFEE4E0EDFFE4E5EBE6F3F7F1E6EBE6EFE0E9FEE4E9F8E0E9FFE473
S121140EE9F8E7F9E7F5ECF8F0F8E0EBFDE2E7F5E7F9EBE9F8E7FEF8F8F1E6EBE6EFB5
S121142CE3EDFEE4E0EDFFE4E3EBECF4F2EBFDEFEFE9F8E7F2EBFDEFF0F1E6EBE6EFBE
S123144AE0EBEBE2EFECF0EAE4EBEFE7E8ECE2E2E0EDF8E7EAECE1E6E7ECE0E0F0ECE0E676

S123146AF4ECFDE5FØECE1E6F4ECFEE5FØECE2E6F4ECFFE5ECECFØEAF7EBECE7EEECFØEAB3
S123148AF2EBF2E5E8ECFØE5E6EBFBFCEØEBFDE2E9F3EØEBEBE2F9F1E6EBE6EFEØEBEBE2D3
S12114AAE5EBE6F3EØEBEBE2E6EBF6E4EØEBEBE2FØECEFE5E1F4F4ECEFE5EAE9EFE5BC
S12114C8F2EBF2E5EØEDEFE5FØECEEE5E1F4F4ECEEE5EAE9EEE5F2EBF2E5EØEDEEE57C
S12314E6F2EBF2E5F4ECEDE4ECECEDE4FBFBFFFBEØE9EEE6FFFBFØEØEDECEDE4E3FCE7FC11
S1231506EØE9F2E6E7FCFØEØEEECEDE4EBFCEFFCEØE9F6E6EFFCFØEØEFECEDE4F3FCF8FCØ3
S1211528EØE9FCE4FØEØECE7EFE3FØEØEØE9EØE4F5FEEØE9E1E4E2FDECECEDEAFØEØ49
S1211544E1E9E1E4E8FDEDECEDEAFØEØE2E9E1E4EEFDEEECEDEAFØEØE3E9E1E4F4FD13
S1211562EFECEDEAFØEØE4E9E1E4FAFDECECECEAFØEØE5E9E1E4EØFEEDECECEAFØEØEE
S121158ØE6E9E1E4E6FEEEECECEAFØEØE7E9E1E4ECFEEFECECEAFØEØE8E9E1E4F2FECE
S123159EECECEEEAFØEØEDECEEEAFØEØE1E9EØE4F2EBF2F6EØE9E1E4FFFEEEECEEEAFØEØCF
S12115BEE1E9E1E4E5FFEFECEBEAFØEØE2E9E1E4EBFFECECEAEAFØEØE3E9E1E4F1FFA1
S12115DCEDECEAEAFØEØE4E9E1E4F7FFEEECEAEAFØEØE5E9E1E4FDFFEFECEAEAFØEØ8C
S12115FAE8E9E1E4E3F8ECECE9EAFØEØE7E9E1E4E9F8EDECE9EAFØEØE8E9E1E4EFF878
S1211618EEECE9EAFØEØEFECE9EAFØEØEØE9E1E4F3F8ECECE8EAFØEØE1E9E1E4FEF838
S1231636EDECE8EAFØEØE2E9E1E4E4F9EEECE8EAFØEØEFECE8EAFØEØFØECEEE9F4ECFØE648
S121165CF2ECEFE9F4ECF1E6E1EDEFE6F2EBFAE9EØE9EEE6FAF9EØEDEFE6F2EBFAE9B2
S1211671EFE9EEE6F2EBFAE9E2EDEFE6F2EBFAE9FØECEDE9E2EBF5F3EBFAE3EDEFE693
S1231692F2EBFAE9EØEDEFE6F2EBFAE9EDF1FØFØF9EFF7FAE4EDEFE6F2EBFAE9EØE9EEE678
S12116B2F2EBFAE9EØEDEFE6F2EBFAE9FØECFØE9ECECECE9EAFBE3EBE7E5E7EDEFE66A
S12316DØF2EBFAE9E3EBFAE5E5EDEFE6F2EBFAE9E4ECEØE6E6EDEFE6F2EBFAE9F2EBFAE964
S12316FØFØECEEE9F4ECFØE6FØECEFE9F4ECF1E6EØE9EEE6F2EBFAE9E8EDEFE6F2EBFAE93E
S123171ØEDF1FØFØF9EFFØFCE9EDEFE6F2EBFAE9EFE9EEE6F2EBFAE9E7EDEFE6F2EBFAE9E3
S121173ØEØEDEFE6E8ECEØE6EEECECE9E3FDE8ECFDE5F2EBFAE9E4ECFDE5F2EBFAE9E4
S121174EFØECF6E9F4ECF4E6FØECF7E9F4ECF5E6E1EDF3E6F2EBFFE9EØE9F2E6FAFD69
S123176CEØEDF3E6F2EBFFE9EFE9F2E6F2EBFFE9E2EDF3E6F2EBFFE9FØECF5E9E2EBF5F39D
S121178CEBFEE3EDF3E6F2EBFFE9EØEDF3E6F2EBFFE9EDF1F4FØF9EFF7FEE4EDF3E63Ø
S12117AAF2EBFFE9EØE9F2E6F2EBFFE9EØEDF3E6F2EBFFE9FØECF8E9ECECF4E9EAFF2C
S12317C8E3EBE7E5E7EDF3E6F2EBFFE9E3EBFAE5E5EDF3E6F2EBFFE9E5ECEØE6E6EDF3E691
S12317E8F2EBFFE9F2EBFFE9FØECF6E9F4ECF4E6FØECF7E9F4ECF5E6EØE9F2E6F2EBFFE9Ø1
S1231808E8EDF3E6F2EBFFE9EDF1F4FØF9EFFØF8E9EDF3E6F2EBFFE9EFE9F2E6F2EBFFE9CE
S1211828E7EDF3E6F2EBFFE9EØEDF3E6E9ECEØE6EEECF4E9E3F9E9ECFDE5F2EBFFE9DC
S1231846E5ECFDE5F2EBFAE9FØECFEE9F4ECF8E6FØECFFE9F4ECF9E6E1EDF7E6F2EBE4EAB1
S1211866EØE9F6E6FAF9EØEDF7E6F2EBE4EAEFE9F6E6F2EBE4EAE2EDF7E6F2EBE4EABD
S1231884FØECFDE9E2EBF5F3EBFAE3EDF7E6F2EBE4EAEØEDF7E6F2EBE4EAEDF1F8FØF9EF89
S12118A4F7FAE4EDF7E6F2EBE4EAEØE9F6E6F2EBE4EAEØEDF7E6F2EBE4EAFØECEØEA8D
S12118C2ECECFCE9EAFBE3EBE7E5E7EDF7E6F2EBE4EAE3EBFAE5E5EDF7E6F2EBE4EA85
S12318EØE6ECEØE6E6EDF7E6F2EBE4EAF2EBE4EAFØECFEE9F4ECF8E6FØECFFE9F4ECF9E642
S1231900EØE9F6E6F2EBE4EAE6EDF7E6F2EBE4EAEDF1F8FØF9EFFØFCE9EDF7E6F2EBE4EA1E
S1211920EFE9F6E6F2EBE4EAE7EDF7E6F2EBE4EAEØEDF7E6EAECEØE6EEECFCE9E3FD85
S123193EEAECFDE5F2EBE4EAE6ECFDE5F2EBFAE9F4ECEFE4ECECEFE4E3EBF2E6EDECEFE4FE
S121195EE3EBF1E7EEECEFE4E3EEEFE8EFECEFE4E3EBEDE9FØEØF4ECEFE4ECECEFE4EF
S121197CE3EBEDE6EDECEFE4E3EBEBE7EEECEFE4E3EBEAE8EFECEFE4E3EBE8E9FØEØF2
S121199AECECF2E5EAFFE4ECF2E5FØECEØF2F4ECECF2FØECE1F2F4ECEDF2FØECE2F262
S12119B8F4ECEEF2FØECE3F2F4ECEFF2EØEDEØF2EØEDE1F2EØEDE2F2EØEDE3F2FØEØ89
S12319D6EDECF2E5F3EBE9E8E5ECF2E5FØECE4F2F4ECFØF2FØECE5F2F4ECF1F2FØECE6F243
S12119F6F4ECF2F2FØECE7F2F4ECF3F2EØEDE4F2EØEDE5F2EØEDE6F2EØEDE7F2FØEØ2F
S1211A14EEECF2E5E7F9E6ECF2E5FØECE8F2F4ECF4F2FØECE9F2F4ECF5F2FØECEAF2C4
S1211A32F4ECF6F2FØECEBF2F4ECF7F2EØEDE8F2EØEDE9F2EØEDEAF2EØEDEBF2FØEØD6
S1211A5ØEFECF2E5E7F9E7ECF2E5FØECFØE4F4ECF9E7FØECF1E4F4ECFAE7FØECF2E4A4
S1231A6EF4ECFBE7FØECF3E4F4ECFCE7FØECF4E4F4ECFDE7FØECF5E4F4ECFEE7FØECF6E474
S1231A8EF4ECFFE7EØEDFØE4EØEDF1E4EØEDF2E4EØEDF3E4EØEDF4E4EØEDF5E4EØEDF6E4F2
S1231AAEEØEDF7E4EØEDF8E4EØEDF9E4EFEDE8F4EFEDE9F4EFEDEAF4EFEDEBF4EFEDECF477
S1211ACEEFEDEDF4EFEDEEF4FØEØEBECEØE6EBECFDE5E8ECE2E6E8ECFFE5FØECE5EA56
S1211AECF4ECFCE6FØECE6EAF4ECFDE6FØECE7EAF4ECFEE6ECECE4EAE5FCF2EBE9EAFF
S1211BØAE1EDFBE6F2EBE9EAEØE9FAE6FØFCEØEDFBE6F2EBE9EAEFE9FAE6F2EBE9EAFF
S1231B28E2EDFBE6F2EBE9EAEDF1FCFØF6EFEØFDE3EDFBE6F2EBE9EAEØE9FAE6F2EBE9EAF3
S1231B48EØEDFBE6F2EBE9EAE7ECEØE6EBECFDE5E2EDEØF3E4EDE1F3EØEDE2F3EØEDE3F33D
S1211B68E4EDFBE6F2EBE9EAEFE9EØE7F2EBE9EAEEECE4EAE1FEF2EBE9EAE4ECE2E6DB
S1211B86F2EBE9EAEØE9FAE6ECFEE6EDFBE6F2EBE9EAEØE9EØF3F8FDEØE9E1F3F8FD73
S1231BA4EØE9E2F3F8FDEØE9E3F3F8FDEFECE4EAFCFEF8FDE3EDFBE6F2EBE9EAFØECE5EA52
S1231BC4F4ECFCE6FØECE6EAF4ECFDE6FØECE7EAF4ECFEE6E7EDFBE6F2EBE9EAEDF1FCFØ2C
S1231BE4F6EFF8FFE8EDFBE6F2EBE9EAEFE9FAE6F2EBE9EAE6EDFBE6F2EBE9EAEDECE4EA28
S1211CØ4E7F8EØEDFBE6F2EBE9EAE9EDFBE6EBECEØE6E7ECFDE5F2EBE9EAF2EBE9EA18
S1231C22EFE9FØE8E1F9EFE9F1E8E1F9EFE9F2E8E1F9F4F1E3EBE8F3FAF1E3EBE8F3F2EØØB
S1231C42FØECFØE8E3EBE8F3F2ECF1E8E3EBE8F3FØECF2E8E3EBE8F3FØECF3E8E3EBE8F3Ø4
S1231C62E5EBE8F3FØECF4E8E3EBE8F3FØECF5E8E3EBE8F3FØECF6E8E3EBE8F3FØECF7E8D4
S1231C82E3EBE8F3E5EBE8F3FØECF8E8E3EBE8F3FØECF9E8E3EBE8F3FØECFAE8E3EBE8F3EA
S1231CA2FØECFBE8E3EBE8F3E5EBE8F3FØECFCE8E3EBE8F3FØECFDE8E3EBE8F3FØECFEE876
S1211CC2E3EBE8F3FØECFFE8E3EBE8F3FØEØFØF5EBFCFCF5FBFEFDF5F6FBFEF5F5FEA2
S1231CEØECEBEBE2EØEBEBE2FØEØEFEDFDE4FØEØEØEDFDE4FØEØE6E6EØE9FDE4FØEBF1E5AC

S1211DØCEFE6E9F3EØEBE6E3E9F7EØEBE9E3EFE6E1FCEØEBF1E2F3EØEBE9F8E7FAFC3D
S1231D1EECECE2E2F5FCE5EBEAE4F8FCEØEDF8E7FBFCEØEDF3E7FØEØE1EDF3E7E3E1F2E711
S1211D3EFØECEFE7E8E6EØE9EEE7E7FDF2F1F1E5E1E9EEE7EEFDEBECEEE7F6F1F1E5D5
S1231D5CE8E9EEE7F5FDEBECEEE7F4F1F1E5E5ECEEE7F8F1F1E5E5EDEAE7E5EDE9E7EEEED6
S1211D7CFCEEEØEEF3EØF4EEF4EEEØEFFAEEF3F1F2EEFØF1F2EEEØEFF1E7EØF1F8FØ58
S1231D9AE4EBF2FCEØEFE4F1F5FØE4EBF2FCEØEFEFECF2E5FEFEE9F1FØFØFDFEEFF1F9FØ2A
S1211DBAE4EEF4FCEØEFFØECEØE6F2EEFØECE1E6F2EEFØECE2E6F2EEFØECFDE5F2EE52
S1231DD6FØECFEE5F2EEFØECFFE5F2EEF4EEEØEFE8F1FØFØE4EBF6FCEØEFFØECFBF2F2EE25
S1231DF8FØECE8E4F2EEEØEFECECF2E5E6F8E4F1FØFØE8F8E4F1FCFØF2E7E4EBFAFCEØEF20
S1231E18EDECF2E5F2F8E4F1F4FØF4F8E5F1FØFØF2E7E4EBFAFCEØEFEEECF2E5FEF8E4F1C8
S1231E38F8FØEØF9E5F1F4FØF2E7E4EBFAFCEØEFFØECEEE5F2EEFØECEFE5F2EEF4EBE8FFB9
S1231E58E5EDEAE7E5EDE9E7EEEEFCEEFCEEF8F1F2EEF4EEEØEFF1E7E1F1FØFØE4EBE2FCCØ
S1231E78EØEFF1E7E2F1F4FØE4EBF6FCEØEFF1E7E2F1FØFØE4EBFAFCEØEFF1E7E4F1F5FØA4
S1231E98E4EBF6FCEØEFF1E7EØF1FØFØE4EBF4FCEØEFF1E7E4F1F4FØE4EBFAFCEØEFF1E782
S1231EB8E2F1FCFØE4EBF8FCEØEFF1E7E3F1F4FØE4EBF8FCEØEFF1E7E3F1FCFØE4EBF8FC39
S1231ED8EØEFF4EBE8FFF1E7EØF1F8FØE5EBFDE1EØF1F8FØE4EBE2F9E4EBE2F9E4EBFBFD3E
S1231EF8F1E7EØF1F8FØE4EBF2FCF4EBE8FFF1E7E1F1FØFØE5EBEBEØE1F1FØFØE4EBE2F931
S1231F18E4EBE2F9E4EBE2F9E4EBE2F9E4EBEAFEF1E7E1F1FØFØE4EBE2FCF4EBE8FFE8F11A
S1231F38FØFØE5EBF7E2E4EBF5FDE8F1FØFØE4EBF6FCF4EBE8FFF1E7E2F1FØFØE5EBFCE3C1
S1231F58E2F1FØFØE4EBE2F9E4EBEFFDF1E7E2F1FØFØE4EBFAFCF4EBE8FFF1E7E2F1F4FØA8
S1231F78E5EBF7E2EAF1FØFØE5EBF7E2E2F1F4FØE4EBE2F9E4EBE2F9E4EBF5FDEAF1FØFØB1
S1211F98E4EBF6FCF4EBE8FFF1E7E4F1F8FØE5EBF7E2E4F1F8FØE4EBE2F9E4EBE2F951
S1231FB8E4EBF5FDF1E7E4F1F8FØE4EBF8FCF4EBE8FFF1E7EØF1FØFØE5EBFDE1EØF1FØFØ42
S1211FD8E4EBE2F9E4EBE2F9E4EBF5FDF1E7EØF1FØFØE4EBF4FCF4EBE8FFE4F1F5FØØC
S1231FF4E5EBFDE1EØEDEFE2EØEDEEE2EØEDEDE2E6EEEAE2E4EBE1FEE4F1F5FØE4EBECFC88
S1232014F4EEE8FFE9F1FØFØE5EBF7E2EØEDF9E4EØEDF8E4EØEDF7E4E6EBEAE2E4EBFEFD1D
S1212034E9F1FØFØE4EBFØFCF4EEE8FFF1E7E2F1FCFØE5EBEBE3E2F1FCFØE4EBE2F9B1
S1232052E4EBE2F9E4EBF2FDF1E7E2F1FCFØE4EBF8FCEØEDEFE6F4EBE8FFF1E7E3F1F4FØEØ
S1212072E5EBEBE3E3F1F4FØE4EBE2F9E4EBE2F9E4EBF2FDF1E7E3F1F4FØE4EBF8FC91
S1212090EØEDF3E6F4EBE8FFF1E7E3F1FCFØE5EBEBE3E3F1FCFØE4EBE2F9E4EBE2F978
S12320AEE4EBF2FDF1E7E3F1FCFØE4EBF8FCEØEDF7E6F4EBE8FFF1E7E4F1F4FØE5EBFCE345
S12120CEE4F1F4FØE4EBE2F9E4EBEFFDF1E7E4F1F4FØE4EBFAFCEØEDFBE6F4EBE8FFØ8
S12120ECFØECFØE3E7EBE5E2FØE8EØEØFØECF1E3E8E7FØECF2E3F8E6FØECF3E3F4E45A
S123210AE7EDEDE7E4EBF8FDFØECFØE3E7EBE5E2F2EEFØECF1E3E8E7F2EEFØECF2E3F8E62F
S123212AF2EEFØECFØE3FØE4F2EEEØEBE3E1FØE4F2EEEØEBE3E1FØE4F2EEEØEBE3E1FØE465
S123214AF2EEFØE7F4EBE8FFFØECFØE3F4ECEBE5FØECF1E3F4ECECE5FØECF2E3F4ECE9E4D8
S123216AFØECF3E3F4ECEAE4FØECF4E3F4ECEBE4FØECF5E3F4ECECE4E6EBFFF9E6EDEDE7BB
S121218AE4EBF5FDFØECFØE3F4ECEBE5FØECF1E3F4ECECE5E6EBE9F8FØECFØE3F2EE71
S12121A8FØECF1E3F2EEFØECE9E4F2EEFØECEAE4F2EEFØECEBE4F2EEFØECECE4F2EE5B
S12321C6F4EBE8FFE4EBE9FDEØEDFEE4EØEDFFE4EØEDEAE5F4EBE8FFE4EBE9FDE4EBE8FF4E
S12321E6EØEDF2E5EØEDEAE5EØEDEFE5EØEDEEE5E8ECE1E6EBECE1E6EFEDF8E7E6E9EFE6BC
S1232206E6F8E7EDEFE6E6E9F3E6EBF8E7EDF3E6E6E9F7E6FØF8E7EDF7E6E4E9FBE6F5F815
S1232226E5EDFBE6E9E9FBE6FAF8EØEDFBE6FØEØFØECFØE3F8E6EØE9F1E3E3F9E4E7E4F91Ø
S1232246E4E3E4EBECFDFØECFØE3F8E6EØE7F6EEEDF9F4EEF4EBE8FFFØECF1E3EØE9FØE3E3
S1232266F6F9FØF6E4FAE1E9FØE5FBF9F1F6E4FAE2E9FØE3EØFAF2F6E4FAE3E9FØE3E4FA9Ø
S1232286F3F6E4EBEFFDF4EEF1F2F2EEF2F2F2EEF3F2F2EEF4EBE8FFF7FAE8EBE9FDF4FAØ6
S12322A8FØEØEFE9F1E5FØFAFØECEAF3F2EEFØECEBF3F2EEFØECECF3F2EEEØEFE5EBE6F386
S12322C8E4F1F5FØE4EBF2FCE2EDE9E7EEEDEAE7EEEEFDFØE4EBFCFCFØEEFØFAE7ECE1EØ48
S12322E8FØECFØE3F4ECEAF3FØECF1E3F4ECEBF3FØECF2E3F4ECECF3EFEDF1E5E5EBE8F32F
S1232306EBF1F4FØE4EBFCFCE2EDE9E7EEEDEAE7EEEEF7FØE4EBF6FCEBECE1EØFØEBF2EØ1A
S1232326E8EBEØF5E4EBE9FDF4EBE8FFE4EBE9FDE9F1FØFØE4EBF4FCEØEBEØE1FØECE3F4ØØ
S1232346EØEBF2EØFØECE9F4EØEBF2EØFØECEAF4EØEBF2EØFØECEBF4EØEBF2EØFØECECF415
S1232366EØEBF2EØFØECEDF4EØEBF2EØFØECEEF4EØEBF2EØEØEBECE1E4F1F5FØE4EBF2FCFE
S1232386EØEBEØE1FØECEØF4EØEBF2EØFØECE1F4EØEBF2EØFØECE2F4EØEBF2EØFØECE3F42A
S12323A6EØEBF2EØFØECE4F2EØEBF2EØFØECE5F4EØEBF2EØFØECE6F4EØEBF2EØFØECE7F4CE
S12323C6EØEBF2EØEØEBEØE1F4EBE8FFEØEDFØE4EØEDE8F4E8ECEØEØFØECEFEØEØEBF2EØ1E
S12323E8FØECEEEØEØEBF2EØEØEBFØEØE9FFF2E7E4F1FØFØE5EBFCE3E4EBEFFDF2E7E4F163
S1212406FØFØE4EBFAFCF4EBE8FFF2E7E4F1F4FØE5EBFCE3E4EBEFFDF2E7E4F1F4FØB5
S1232424E4EBFAFCF4EBE8FFF2E7E4F1F8FØE5EBFCE3E4EBEFFDF2E7E4F1F8FØE4EBFAFCAE
S1212444F4EBE8FFFØECFØE3F4ECFØEØFØECF1E3F4ECF1EØE8F3EØEBEBE2EØEBEBE2E5
S1232462EØEBEBE2EØEBEBE2EØEBEBE2EØEBEBE2EØEBEBE2EØEBEBE2EØEBEBE2EØEBEBE298
S1232482EØEDF1EØE8F7EØEBFDE2E4EBE9FDF4EBE8FFEØEBEBE2FØECEØFEF2EEFØECE1FEA7
S12324A2F2EEFØECE2FEF2EEFØECE3FEF2EEEØEFFØECE4FEF2EEFØECE5FEF2EEFØECE6FE31
S12324C2F2EEFØECE7FEF2EEEØEFFØECE8FEF2EEFØECE9FEF2EEFØECEAFEF2EEFØECEBFEF8
S12324E2F2EEEØEFFØECECFEF2EEFØECEDFEF2EEFØECEEFEF2EEFØECEFFEF2EEE5EBE9EØF9
S1232502F2ECFØFEF2EEFØECF1FEF2EEFØECF2FEF2EEFØECF3FEF2EEEØEFFØECF4FEF2EE8A
S1232522F2ECF5FEF2EEFØECF6FEF2EEFØECF7FEF2EEEØEFFØECF8FEF2EEFØECF9FEF2EE51
S1232542F2ECFAFEF2EEFØECFBFEF2EEEØEFFØECFCFEF2EEFØECFDFEF2EEFØECFEFEF2EE18
S1232562F2ECFFFEF2EEE5EBE2EØF2ECEØFFF2EEFØECE1FFF2EEFØECE2FFF2EEFØECE3FF7A
S1212582F2EEEØEFFØECE4FFF2EEFØECE5FFF2EEFØECE6FFF2EEFØECE7FFF2EEEØEF37
S12325AØF2ECE8FFF2EEFØECE9FFF2EEFØECEAFFF2EEFØECEBFFF2EEEØEFFØECECFFF2EEØF

S12325CØFØECEDFFF2EEFØECEEFFF2EEFØECEFFFF2EEE5EBEØEØFØECFØFFF2EEFØECF1FFF8
S12325EØF2EEFØECF2FFF2EEFØECF3FFF2EEEØEFFØECF4FFF2EEFØECF5FFF2EEFØECF6FF9D
S12126ØØF2EEFØECF7FFF2EEEØEFFØECF8FFEØEBF2EØFØECF9FFF2EEFØECFAFFF2EE7E
S123261EFØECFBFFF2EEEØEFFØECFCFFF2EEFØECFDFFF2EEFØECFEFFF2EEFØECFFFFF2EE31
S121263EFØEBFØEØFØEØE4EBEBFBFØECFØE3F4ECE9E4FØECF1E3F4ECEAE4FØECF2E3DF
S123265CF4ECEBE4FØECF3E3F4ECECE4E6EBFFF9FØECF4E3F4ECFØE3FØECF5E3F4ECF1E3B2
S123267CFØECF6E3F4ECF2E3FØECF7E3F4ECF3E3FØECF8E3F4ECF4E3FØECF9E3F4ECF5E338
S123269CFØECFAE3F4ECF6E3FØECFBE3F4ECF7E3FØECFCE3F4ECF8E3FØECFDE3F4ECF9E346
S12326BCFØECFEE3F4ECFAE3FØECFFE3F4ECFBE3E6EFE3EFE3EFE3EFFØEØE1EØE8E3E1EØ9F
S12326DCECE7EØE5F4ECEBE5EFE5EØE5F4ECECE5FØECEBE5ECE7EØE5F4ECEBE5FØECECE5A7
S12326FCEØE5F4ECECE5FØEØE4EBE4FDE4EBE4FDE4EBE4FDE4EBE4FDE4EBE4FDE4EBE4FD54
S123271CE4EBE4FDE4EBE4FDE4EBE4FDE4EBE4FDE4EBE4FDE4EBE4FDE4EBE4FDE4EBE4FD19
S123273CE4EBE4FDE4EBE4FDFØE7FØEØFØE4F2EEE3EFE8FDFØEØEØEDEDE7E7FEE2EDEDE7ØE
S123275CE7FEE4EDEDE7E7FEE5EDEDE7E7FEE6EDEDE7E7FEE7EDEDE7E7FEE8EDEDE7E7FEB8
S123277CE9EDEDE7E7FEEBEDEDE7E7FEECEDEDE7E7FEEØEDECE7EEFEEØEDEDE7E1EDECE7B9
S123279CE5EDEAE7E5EDE9E7EEEEFØECECE7F2EEFØECEDE7F2EEFØECEEE7F2EEFØECEFE798
S12127BCF2EEFØEØEØEDEAE7E2EDE9E7E5EBE8E6EEEEFØE2FØECF2E7E1EBF6FBEEEE76
S12127DAFØECF3E7F2EEEDEDEAE7EØEDE9E7EEEEEAEDEAE7EØEDE9E7EEEEEAEDEAE75A
S12127F8EØEDE9E7EEEEFØEØEDEDEAE7EØEDE9E7EEEEEAEDEAE7EØEDE9E7EEEEFØEØ61
S1212816FØECFØE3E2EFFØECF1E3E2EFFØECF2E3E2EFFØECF3E3E2EFFØECF4E3E2EF16
S1212834FØECF5E3E2EFFØECF6E3E2EFFØECF7E3E2EFFØECF8E3E2EFFØECF9E3E2EFDF
S1212852FØECFAE3E2EFFØECFBE3E2EFFØECFCE3E2EFFØECFDE3E2EFFØECFEE3E2EFA8
S1232870FØECFFE3E2EFFØE7FØEØFØECFØE3E2EFFØECF1E3E2EFFØECF2E3E2EFFØECF3E3D9
S1212890E2EFFØECF4E3E2EFFØECF5E3E2EFFØECF6E3E2EFFØECF7E3E2EFFØE7FØEØ98
S12128AEFØECFØE3E2EFFØECF1E3E2EFFØECF2E3E2EFFØECF3E3E2EFFØECF4E3E2EF7E
S12328CCFØECF5E3E2EFFØE7FØEØFØECFØE3E2EFFØECF1E3E2EFFØECF2E3E2EFFØECF3E387
S12128ECE2EFFØECF4E3E2EFFØE7FØEØFØECFØE3E2EFFØECF1E3E2EFFØECF2E3E2EF4B
S123290AFØECF3E3E2EFFØE7FØEØE5EBF6E4FØECF1E7E4E8F3E7F5FCFØECFØE7E4E8F2E78C
S121292AFØEØE1EDF3E7E3EDF2E7FØECECE7E1EBF6FBE5EBE8E6FØECEDE7E1EBF6FEF3
S1232948E5EBE8E6FØECEEE7E1EBF6FBE5EBE8E6FØECEFE7E1EBF6FBE5EBE8E6FØECEDE7Ø4
S1232968E8E6EFE6EØE9EDE7FDFDEØE9ECE7FDFDFØEØE7F1FØFØFØE4E1EBF6FBE5EBE8E6C4
S1232988E3EFEFE6FFFDFØEØE8E2F4ECEEE4FØECEAE7F4ECF5E7FØECE9E7F4ECF4E7FØE8C4
S12129A8F2ECF3E7F4ECF7E7FØECF2E7F4ECF6E7EFECF4E7EØFFE9FFF1F1FCE8F3E7ØA
S12329C6F4ECF7E7FØECF2E7F4ECF6E7FØECF7E7EØE5EFE3EØEDF7E7FØF1EØE5F4ECF8E75E
S12329E6F6FFF5EEEØE8F2F1FCE8F3E7F4ECF3E7FAF1FCE8F2E7F4ECF2E7ECE7FØECF2E7EC
S1232A06EØE5F4ECF2E7FØECF3E7EØE5F4ECF3E7FØECF3E7ECE8F7E7F4ECF3E7FØECF2E7CC
S1232A26ECE8F6E7F4ECF2E7ECE7FØECF5E7E1E5F4ECF5E7FØECF4E7E1E5F4ECF4E7EFE8C8
S1212A46F5EBF4E8FØECEEE4E8E6FØEØF1F2F4ECEDE4ECECEDE4F2EBE1E9E6EBEDE5E1
S1232A64E6EBF6E5FØECE3E7E6EBEBE8FØECE4E7E6EBEBE8FØECE5E7E6EBF1E8FØECE6E7FD
S1232A84E6EBF4E8FØECE7E7E6EBF7E8FØECE8E7E6EBFAE8E6EBF9FØE6EBECF2F2EBEFE9AE
S1212AA4F1FCF4ECEDE4EDECEDE4F2EBE1E9FØECEØE5E6EBE5E8FØECE1E5E6EBE8E8A9
S1232AC2E6EBE3E6FØECE2E5E6EBEBE8FØECE3E5E6EBF1E8E6EBE4E7FØECE4E5E6EBF7E8CD
S1212AE2FØECE5E5E6EBFAE8E6EBFBF2E6EBFBF1F2EBEFE9F1F2F4ECEDE4EEECEDE4ØA
S1232BØØF2EBE1E9FØECE5E2E6EBE5E8FØECE6E2E6EBE8E8FØECE7E2E6EBEBE8FØECE3E295
S1232B2ØE6EBEBE8FØECE9E2E6EBF1E8FØECEAE2E6EBF4E8FØECEBE2E6EBF7E8FØECECE241
S1212B4ØE6EBFAE8E6EBFBF1E6EBEAF3F2EBEFE9F1F2F4ECEDE4EFECEDE4F2EBE1E9B9
S1232B5EFØECFØE4E6EBE5E8FØECF1E4E6EBE8E8FØECF2E4E6EBEBE8FØECF3E4E6EBEEE8Ø3
S1232B7EFØECF4E4E6EBF1E8FØECF5E4E6EBF4E8FØECF6E4E6EBF7E8FØECF7E4E6EBFAE8A3
S1212B9EE6EBEAF1E6EBF9F3F2EBEFE9F2F2F4ECEDE4ECECEDE4F2EBE1E9FØECEØE472
S1232BBCE6EBE5E8FØECE1E4E6EBE8E8E6EBE3E6FØECE2E4E6EBEBE8FØECE3E4E6EBF1E8E5
S1232BDCE6EBE4E7FØECE4E4E6EBF7E8FØECE5E4E6EBFAE8E6EBFBF1E6EBE8F4E6ECF8E277
S1212BFCE6ECE8E3F2EBEFE9F2F2F4ECEDE4EDECEDE4F2EBE1E9FØECEFE6E6EBE5E83Ø
S1232C1AFØECF3E6E6EBE8E8FØECF7E6E6EBEBE8FØECFBE6E6EBEEE8FØECFCE4E6EBF1E813
S1212C3AE6EBE4E7F3F1E6EBF7E8FØF1E6EBFAE8E6EBFBF1E6EBE8F4F2EBEFE9F2F2B1
S1232C58F4ECEDE4EEECEDE4F2EBE1E9FØF1EØE9EBE6E5EBE4F3E6EBE5E8FØF1EØE9F2E61Ø
S1232C78E5EBE4F3E6EBE8E3FØF1EØE9F6E6E5EBE4F3E6EBEBE8E6EBEEE6E6EBF9E6FØF1E9
S1232C98EØE9FAE6E5EBE4F3E6EBF4E8E6EBEFE7F3F2F4ECEDE4FØF1EFECEDE4E5EBE4F3AA
S1232CB8E6EBFAE8E6EBFBF1E6EBE8F4F2EBEFE9F1F1FØEØEFE9F1E5F6EBFDEØEØE9ECF382
S1232CD8F6FBEØE9EBF3F6FBEØE9EAF3F6FBE6EDFCE4FFFBFØECFCE4EFF4F4ECFCE4FEF5B9
S1212CF8FFFBEØEDFCE4EØEDFCE5EØEDFBE5EØEDFAE5EØEDF9E5EØEDF8E5EØEDF7E5ØE
S1232D16EØEDF6E5EØEDF5E5EØEDF4E5EØEDEDE6EØEDECE6EØEDEBE6EØEDEAE6EØEDE9E68E
S1212D36EØEDE8E6EØEDE7E6EØEDE6E6E5F1F8FØEFE7F1F1F8ECECF3F4ECECF3FØF1D4
S1212D54F6ECEBF3F4ECEBF3FØF1F8ECEAF3F4ECEAF3EFE3F7FDF5EBE7F9EFE7F1F14Ø
S1232D72F8ECE7E6F4ECE7E6FØF1F8ECE8E6F4ECE8E6EFE3E6FFF1E7FØE4F4ECE6E6E3EFC1
S1232D92FØE4F4ECE7E6E3EFFØE4F4ECE8E6E3EFFØE4F4ECE9E6E3EFFØE4F4ECEAE6E3EFCE
S1232DB2FØE4F4ECEBE6E3EFFØE4F4ECECE6E3EFFØE4F4ECEDE6E3EFFØE7ECE7FØECFCE56E
S1232DD2F8E8EDE6E6E5F4ECFCE5FØECFBE5F8E8ECE6E6E5F4ECFBE5FØECFAE5F8E8EBE639
S1212DF2E6E5F4ECFAE5FØECF9E5F8E8EAE6E6E5F4ECF9E5FØECF8E5F8E8E9E6E6E5ØF
S1232E1ØF4ECF8E5FØECF7E5F8E8E8E6E6E5F4ECF7E5FØF1F8E8F8E5E6E5F4ECF6E5FØF1F1
S1212E3ØF8E8F5E5E6E5F4ECF5E5FØF1F8E8F4E5E6E5F4ECF4E5F5EBE3F5F5EBE3F5B3
S1232E4EEØEDF1E5EØEDEAF3ECE7FØECF9E5F8E8EFE2E6E5F4ECEFE2FØECF8E5F8E8EEE2FC

S1212E6EE6E5F4ECEEE2FØECF7E5F8E8EDE2E6E5F4ECEDE2FØECF6E5F8E8ECE2E6E5B6
S1232E8CF4ECECE2E8E6EØEAE8E2F4ECE7F4FØECF5E5F8E8EBE2E6E5F4ECEBE2E8E6EØEAE4
S1232EACE8E2F4ECE6F4FØECF4E5F8E8EAE2E6E5F4ECEAE2E8E6EØEAE8E2F4ECE5F4FØF1AA
S1232ECCF8E8E9E2E6E5F4ECE9E2E8E6EØEAE8E2F4ECE4F2FØF1F8E8E8E2E6E5F4ECE8E2A9
S1232EECE8E6EØEAE8E2F4ECE3F4FØF1F8E8E7E2E6E5F4ECE7E2E8E6EØEAE8E2F4ECE2F493
S1212FØCF2F1F8E8E6E2E6E5F4ECE6E2E8E6EØEAE8E2F4ECE1F4FØF1F8E8E5E2E6E53D
S1212F2AF4ECE5E2E8E6EØEAE8E2F4ECEØF4ECE7FØECF9E5F8E8F9E4E6E5F4ECF9E4F6
S1232F48FØECF8E5F8E8F8E4E6E5F4ECF8E4FØECF7E5F8E8F7E4E6E5F4ECF7E4FØECF6E5B9
S1212F68F8E8F6E4E6E5F4ECF6E4E8E6EØEAE8E2F4ECEEF4FØECF5E5F8E8F5E4E6E5AA
S1232F86F4ECF5E4E8E6EØEAE8E2F4ECEDF4FØECF4E5F8E8F4E4E6E5F4ECF4E4E8E6EØEAC3
S1232FA6E8E2F4ECECF4FØF1F8E3F3E4E6E5F4ECF3E4E8E6EØEAE8E2E8E2F4ECEBF4FØF197
S1232FC6F8E8F2E4E6E5F4ECF2E4E8E6EØEAE8E2F4ECEAF4FØF1F8E8F1E4E6E5F4ECF1E47A
S1232FE6E8E6EØEAE8E2F4ECE9F4FØF1F8E8FØE4E6E5F4ECFØE4E8E6EØEAE8E2F4ECE8F476
S12130Ø6E4F8EØEDE6E7EØEDE7E7EØEDE6E7EØEDE5E7EØEDE4E7EØEDE3E7E6EBFEEØ84
S121302 4E6EBFEEØE6EBFEEØE6EBFEEØE6EBFEEØE6EBFEEØFDF8FØEØECE7FØECF8E5CE
S1233042F8E8E8E7E6E5F4ECE8E7FØECF7E5F8E8E7E7E6E5F4ECE7E7FØECF6E5F8E8E6E7FE
S1213062E6E5F4ECE6E7FØECF5E5F8E8E5E7E6E5F4ECE5E7FØECF4E5F8E8E4E7E6E5DØ
S121308ØF4ECE4E7FØF1F8E8E3E7E6E5F4ECE3E7E9FAFØEØFØECE5E2E9EFF4ECEØF4A1
S12130 9EFØECE6E2E9EFF4ECE1F4FØECE7E2E9EFF4ECE2F4FØECE8E2E9EFF4ECE3F477
S12130BCFØECE9E2E9EFF4ECE4F2FØECEAE2E9EFF4ECE5F4FØECEBE2E9EFF4ECE6F449
S12130DAFØECECE2E9EFF4ECE7F4FØECFØE4E9EFF4ECE8F4FØECF1E4E9EFF4ECE9F4ØD
S12130F8FØECF2E4E9EFF4ECEAF4FØECF3E4E9EFF4ECEBF4FØECF4E4E9EFF4ECECF4D8
S1213116FØECF5E4E9EFF4ECEDF4FØECF6E4E9EFF4ECEEF4FØEØE6EBEDE5E6EBF8E5D8
S1233134E6EBE3E6E8EBEEE6E6EBF9E6E6EBE4E7E6EBEFE7E6EBFAE7E6EBFBF1E6EBE8F429
S1233154EAECECE3FØEØE8ECFØE2E9ECFØE2EØEDF1E2E6ECF2E2E9ECF2E2FØEØE8ECF4E22A
S1213174E9ECF4E2EØEDF5E2E8ECF6E2E9ECF6E2FØEØE8ECF8E2E9ECF6E2EØEDF9E2BC
S1233192E8ECFAE2E9ECFAE2FØEØE8ECFCE2E9ECFCE2EØEDFDE2E8ECFEE2E9ECFEE2FØEØ9E
S12131B2E8ECEØE3E9ECEØE3EØEDE1E3E8ECE2E3E9ECE2E3FØEØE8ECE4E3E9ECE4E3Ø1
S12131DØEØEDE5E3E8ECE6E3E9ECE6E3FØEØE8ECE8E3E9ECE8E3EØEDE9E3E8ECEAE3C4
S12331EEE9ECEAE3FØEØE8ECECE3E9ECECE3EØEDEDE3E8ECEEE3E9ECEEE3FØEØE5F1FØF096
S123320EFDF8E5F1F4FØFDF8E5F1F8FØFDF8E5F1FCFØFDF8E6F1FØFØFDF8E6F1F4FØFDF832
S123322EE6F1F8FØFDF8E6F1FCFØFDF8FØE7FEF5EAF9E4E4E5E4E3EFE4E4E5E4EAE4E3EFCF
S123324EE8E4E9E4FØEØFDF5F6F9E4E4E5E4E3EFE4E4E5E4E6E4E3EFE8E4E9E4FØEØFCF528
S123326EE2FAE8E4E5E4E3EFE8E4E5E4E6E4E3EFE4E4E5E4FØEØFBF5EEFAE4E4E5E4E3EF2C
S123328EE4E4E9E4E6E4E3EFE8E4E9E4FØEØFAF5FAFAE4E4E5E4E3EFE8E4E5E4E6E4E3EFØB
S12332AEE8E4E5E4FØEØF9F5E6FBE4E4E5E4E3EFE4E4E5E4EAE4E3EFE4E4E5E4FØEØF8F5E6
S12332CEF2FEE4E4E9E4E3EFE4E4E5E4EAE4E3EFE4E4E5E4FØEØF7F5FEFEE4E4E5E4E3EFAE
S12332EEE4E4E5E4E6E4E3EFE4E4E5E4FØEØF6F5EAFCE8E4E9E4E3EFE4E4E9E4EAE4E3EFBD
S123330EE4E4E5E4FØEØF5F5F6FCE4E4E5E4E3EFE4E4E5E4E6E4E3EFE8E4E5E4FØEØF4F58Ø
S123332EE2FDE4E4E9E4E3EFE4E4E5E4E6E4E3EFE8E4E5E4FØEØF3F5EEFDE4E4E9E4E3EF69
S123334EE8E4E5E4EAE4E3EFE4E4E5E4FØEØF2F5FAFDE8E4E9E4E3EFE4E4E5E4E6E4E3EF4F
S123336EE4E4E5E4FØEØF1F5E6FEE8E4E5E4E3EFE4E4E5E4E6E4E3EFE4E4E9E4FØEØFØF532
S123338EF2FEE8E4E9E4E3EFE8E4E9E4EAE4E3EFE4E4E5E4FØEØE4E4E5E4E3EFE4E4E9E42E
S12133AEE6E4E3EFE4E4E5E4FØEØE4E4E5E4E3EFE8E4E9E4E6E4E3EFE8E4E9E4FØEØFF
S12333CCE6EBFAE8FCF1E6EBE5E8FAF1E6EBE8E8E5F1F8FØE6EBFCEEE5F1FCFØE6EBFCEE1D
S12133ECF2F2F4ECEDE4EFECEDE4F6EBEEFØFØECEØE6E6EBF1E8FØECE1E6E6EBF4E823
S121342AFØECE2E6E6EBF7E8E6EBFBF1E6EBE8F4FØEØE6EBF9E6E6EBE4E7E6EBEFE71F
S1213428E6EBFBF1E6EBE8F4FØEØEAECF2E2EAECF6E2EAECFAE2EAECFEE2EAECE2E3ED
S1213446E6ECE8E3EAECEAE3EAECFØE2F7FCEAECF2E2EAECF8E2EAECFAE2EAECFEE2CB
S1213464EAECE2E3EAECE6E3E6ECEAE3EAECFØE2F7FCEAECF2E2EAECF6E2EAECFAE2C8
S1213482EAECFEE2EAECE2E3EAECE6E3EAECEAE3EAECFØE2F7FCEAECFØE2E6ECF4E2AA
S12134AØEAECF8E2EAECFCE2EAECEØE3EAECE4E3EAECE8E3F7FCEAECFØE2EAECF4E288
S12134BEEAECF8E2E6ECFCE2EAECEØE3EAECE4E3EAECE8E3F7FCEAECFØE2EAECF4E26E
S12134DCEAECF8E2EAECFCE2E6ECEØE3EAECE4E3EAECE8E3F7FCEAECFØE2EAECF4E25Ø
S12134FAEAECF8E2EAECFCE2EAECEØE3E6ECE4E3EAECE8E3F7FCEAECFØE2EAECF4E232
S1233518EAECF8E2EAECFCE2EAECEØE3EAECE4E3EAECE8E3F7FCEFE9EØE7FDFCE6ECECE325
S1213538FØEØEAECECE3FØEØF1E7EØF1FØFØEØEDEBE5E6EBF5F5E1EDEBE5E6EBF5F5F2
S1233556E2EDEBE5E6EBF5F5E3EDEBE5E6EBF5F5FCE7FØEØEØEDECE5E6EBF6F7E1EDECE5FA
S1233576E6EBF6F7E2EDECE5E6EBF6F7E3EDECE5E6EBF6F7E4EDECE5E6EBF6F7E5EDECE5B3
S1233596E6EBF6F7E6EDECE5E6EBF6F7E7EDECE5E6EBF6F7E8EDECE5E6EBF6F7E9EDECE583
S12335B6E6EBF6F7EAEDECE5E6EBF6F7EBEDECE5E6EBF6F7ECEDECE5E6EBF6F7EDEDECE553
S12335D6E6EBF6F7EEEDECE5E6EBF6F7EFEDECE5E6EBF6F7FØEØE6EBE9F8FØECE9E4F4E43E
S12335F6E3EFFØECEAE4F4E4E3EFFØECEBE4F4E4E3EFFØECECE4F4E4E3EFFØEØE6EBE5FD5D
S1233616EAECEBE5E7ECEBE5E6EBF9FBE6EBE4F9F4ECE9E4E6EBE4F9F4ECEAE4E6EBE4F91D
S1233636F4ECEBE4E6EBE4F9F4ECECE4E6EBFBFCFØEØE3F7FØF1E2F5E3F3EAF9EBF9E8F4CØ
S1233656E3F7E2F5E3F3FØF9F1F9E4F4E3F7E2F5E3F3F6F9F7F9E2F4E3F7E2F5E3F3FCF966
S1233676FEF9E1F4FEF9FØEØE6EBE5FDE6EBEDFBE6ECEBE5E7ECEBE5E6EBF9FBE1F3E3F779
S1213696E3F3E4F3E4F7EØEBEFE3E6ECEBE5EBECEBE5E6EBF9FBFØECE9E4E6EBEAFC7F
S12336B4FØECEAE4E6EBEAFCFØECEBE4E6EBEAFCFØECECE4E6EBEAFCE4F3E4F7EØEBEFE37D
S12336D4E6EBFBFCFØEØE4F3E4F7E6EBF3FCE6EBF7FCF3F1E6EBEAFCE6EBEAFCFØEØE1F3ØE
S12336F4E3F3E4F3E4F7E6EBF3FCE6EBF7FCFØECEBE5E6EBEAFCFØECECE5E6EBEAFCFØEØØF

S1233714E6EBFØFCE6EBFØFCE6EBFØFCE1E5EFE3F7FCE1F3E3F7E3F3FØEØE1F7E3F7E3F3FC
S1233734FØEØEØE9FØE5E5FDE6F3E3F3E1F3E4F3E6F7EØF7FØEØEØF3EØEBEFE3FØEØF2F21D
S1233754F4ECEDE4EØE9EDE4F1FDF7EEF3E2EFECEDE4F5FDF6F1ECE7EFE3FØEØFØECF8F29C
S1213774E7EBE5E2FØECF9F2E6E7FØECFAF2F8E6EFEDEDE4F1F2FCE8EDE4F4ECEDE488
S1233792ECECEDE4F1FEEDECEDE4F1FFF7EBEDEØEEECEDE4EØEBEBE2EØEBE9E3FCE2EFE5A8
S12337B2F4ECFAF2F7EBEDEØFØECF9F2E1F4F4ECF9F2E8E7FØF5E7FFF7EBEDEØFØECF8F2Ø2
S12337D2E1F4F4ECF8F2EDFFE7EBE5E2F7EBEDEØEEECEDE4EØEBEBE2EØEBE9E3FFE6EFE56D
S12137F2F4ECFAF2F7EBEDEØFØECF9F2EFF4F4ECF9F2E8E7FEF5EDF8FØECF8F2EFF475
S1233810F4ECF8F2EBF6E7EBE5E2EAECF8F2EBECF8F2FØECF8F2FØE4F4ECEDE4EØEBE3E1FC
S1233830F2E4F4ECEEE4E2EBE3E1FØE4F4ECEFE4EØEBE3E1FØE4FØE7E6EBFAE8FØECF8F22E
S1233850E6EBE5E8FØECF9F2E8EBE8E8FØECFAF2E6EFEBE8E6EFEEE6FØECEDE4E6EBF1E8E8
S1233870F2ECEEE4E6EBF4E8F2ECEFE4E6EBF7E8E6EFFBF1E8EBE8F4FØEØFØF5EDFAF1F58E
S1233890EFFAF2F8F1FAF3E7FØEØFØE7FØEØF1E7FØEØF2E7FØE8EFEDEDE4F1F2FCE8EDE471
S12138BØF4ECEDE4ECECEDE4FEFCEDECEDE4E7FEEFECEDE4ECFCFØECE8E8E6EBE5E635
S12338CEFØECE9E8E6EBE8E8FØECEAE8E6EBEBE8FØECEBE8E8EBEEE8FØECECE8E6EBF1E88C
S12338EEFØECEDE8E6EBF4E8FØECEEE8E6EBF7E8FØECEFE8E8EBFAE8E6EBFBF1EEECEDE42C
S12139ØEECEBEBE2EØEBEDE8FØEØF1F2F4ECEDE4EFECEDE4F3FCECFCEØF1F8FØEØF3F1
S123392CEØEBEDE3E4EBE2F9E4EBE2F9EØF7FØEØFØECEFE8E1F4F4ECEFE8EAE9EFE8E3FB1A
S121394CEØEDEFE8FØECEEE8E1F4F4ECEEE8EAE9EEE8E3F5EØEDEEE8FØECEDE8E1F4C8
S121396AF4ECEDE8EAE9EDE8E3F5EØEDEFE8FØECECE8E1F4F4ECECE8EAE9ECE8E3FBAØ
S1213988EØEDECE8E3FBFØECEFE8EFF4F4ECEFE8FEF5E3FBE9EDEFE8FØECEEE8EFF43E
S12139A6F4ECEEE8FEF5E3FBE9EDEEE8FØECEDE8EFF4F4ECEDE8FEF5E3FBE9EDEDE8Ø7
S12339C4FØECECE8EFF4F4ECECE8FEF5E3FBE9EDECE8E3FBFAF1E6EBE6EFE4ECFØE5EØF336
S12339E4E6F7E9F7FØECF1EAF4ECE6F3FØECF2EAF4ECE7F3E7EBF1EEFØECE9E7E8E6F8F1ØA
S1213AØ4F2E5EØE9EAE7E8F8F1EBFCE5E1E9EAE7EDF8F7EBFCE7FØECE9E7F4ECE8F3EF
S1233A22FØECEAE7F4ECE9F3ECEBEBEØF7EBFCE7EAECEAE7EBECEAE7FØECEAE7FØE8ECEØ25
S1233A42E7EFF1EEFØECE9E7E8E7FØECEAE7F8E6F7EBFCE7FØECEAE7E8E6FCF1F2E5FØE4D1
S1233A62F2EEE3EFFØE4F2EEE3EFFØE4F2EEE3EFFØE4F2EEE3EFF2E4F2EEE3EFFØE4F2EEC1
S1233A82E3EFFØE4F2EEE3EFFØE4F2EEE3EFFØE4F2EEE3EFFØE4F2EEE3EFFØE4F2EEE3EFBD
S1213AA2FØE4F2EEE3EFFØE4F2EEE3EFFØE4F2EEE3EFFØE4F2EEE3EFFØE4F2EEE3EF64
S1233ACØF7EBFCE7E7EBF1EEFØECE9E7F4ECE6F3FØECEAE7F4ECE7F3F7EBFCE7FØECEAE7CE
S1213AEØF4ECEDE4FØECE6F3F4ECE9E7FØECE9F3F4ECEAE7FØECEDE4E8E6FAF1F2E5Ø6
S1233AFEEØEBEEEØEØEBEEEØEØEBEEEØEØEBEEEØEØEBEEEØEØEBEEEØEØEBEEEØEØEBEEEØDC
S1233B1EEØEBEEEØEØEBEEEØEØEBEEEØEØEBEEEØEØEBEEEØEØEBEEEØEØEBEEEØEØEBEEEØBE
S1233B3EEF7EBFCE7FØECEAE7E4EØF7EBFCE7E7EBF1EEE7EBF1EEF7EBFCE7ECECEAE7F6FDA5
S1233B5EEDECEAE7FDFDECE4E6F1F7EBFCE7EDECEAE7E1FEEEE4E6FDF7EBFCE7EDE4E6FD70
S1233B7EF7EBFCE7EFE4E6FDF7EBFCE7FØE4E1F4F4E4F7EBFCE7F7EBFCE7FØECEAE7F4E453
S1233B9EF7EBFCE7F2ECE6F3EØE5F4ECEBE5FØECE7F3EØE5F4ECECE5EAECEBE5E7ECEBE59F
S1213BBEE6EBF9FBECECE7F3F1FFE6EBE4F9F4ECE9E7E6EBE4F9F4ECEAE7E6EBE4F913
S1213BDCE6EBE4F9FDFFE6EBE4F9E6EBE4F9E6EBE4F9F4ECE9E7E6EBE4F9F4ECEAE7Ø4
S1213BFAFØECE7F3E1F4F4ECE7F3EØE9E7F3EBF8FØECE6F3E1F4F4ECE6F3EBF8FØEØE6
S9Ø3ØØØØFC

While the principles of this invention have been described in connection with specific embodiments, it should be understood clearly that these descriptions are made only by way of example and are not intended to limit the scope of the invention.

We claim:

1. An apparatus connectable by a telephone line to a central computer system for monitoring a water treatment system including:

a first input port for receiving a first signal representing a volumetric flow rate at which water is flowing through the system;

a second input port for receiving a second signal representing an unacceptable physical characteristic of the water;

a processing circuit including a microprocessor programmable for receiving the first signal and totaling system subsequent to a defined event;

the processing circuit further including a read time clock for continuously computing time;

a power supply for providing electrical power to the apparatus;

the apparatus being arranged for initiating a call to the computer system upon the occurrence of either a first condition or a second condition;

the first condition including the flow of a predetermined total volume of water through the treatment system subsequent to the defined event;

the second condition including the co-existence of said first signal and said second signal.

2. The apparatus of claim 1 wherein a call is initiated only if the second condition persists for a predetermined time.

3. The apparatus of claim 1 wherein a message signal is transmitted to the computer system during a call and the message signal includes a first set of data for identifying the location of the apparatus and a second set of data for indicating the time at which the cell was initiated.

4. The apparatus of claim 3 wherein the message signal further includes a third set of data for indicating the total volume of water which has flowed through the water treatment system subsequent to the defined event.

5. The apparatus of claim 1 wherein the first signal is manifested by a series of electrical pulses, the frequency of which per unit time is indicative of the volumetric flow rate of water through the system and wherein the second signal is binary to define a change of state of electrical contacts.

6. An apparatus connectable by a telephone line to a central computer system for monitoring a water deionizing system including:

a power supply for providing electrical power to said apparatus;

a first input port for receiving a first signal representing a volumetric flow rate at which water is flowing through the system;

a second input port for receiving a second signal representing a physical characteristic of the water flowing through the system;

a processing circuit coupled to the power supply and connected to process signals received at the first input port and at the second input port, the processing circuit including a real time clock for computing the lapse of time;

the processing circuit being arranged for initiating a call to the computer system and transmitting a message signal thereto upon the occurrence of and one of a first condition, a second condition, a third condition or a fourth condition;

the first condition including the flow of a total volume of water through the deionizing system which is equal to a predetermined volume of water;

the second condition including the co-existence of the first signal and the second signal for a predetermined time interval;

the third condition including the lapse of a predetermined time interval subsequent to the refurbishment of tanks used to deionize the water;

the fourth condition including manual actuation of the apparatus to initiate the call.

7. The apparatus of claim 6 wherein in the event of non-completion of an initiated call, the apparatus repetitively initiates message calls until a call to the computer system is completed.

8. The apparatus of claim 6 wherein the call is made upon the occurrence of the first condition and the message signal comprises an alarm report whereby an alarm signal occurs at said computer system.

9. The apparatus of claim 6 wherein the message call is made upon the occurrence of the third condition and the message signal comprises a status report including:

a first set of data for identifying the location of the apparatus;

a second set of data for indicating the time at which the message call was initiated;

a third set of data for indicating the total volume of water which has flowed through the treatment system subsequent to a defined event, and;

a fourth set of data for indicating the volume of water which has flowed through the treatment system since the preceding status report.

10. A method for monitoring a water treatment system including:

generating a first signal representing the rate at which water flows through the treatment;

generating a second signal representing a physical characteristic of the water flowing through the treatment system;

totaling the volume of water which has flowed through the treatment system subsequent to a defined event;

initiating a call to a central computer if (a) the total volume of water is equal to a predetermined volume of water, or if (b) the actual physical characteristic represented by the second signal becomes equal to a predetermined physical characteristic and the first signal and the second signal coexist.

11. The method of claim 10 wherein the first signal an electrical signal and the physical characteristic is conductivity.

12. The method of claim 10 wherein the defined event includes the refurbishing of the medium used to treat water flowing through the system and the predetermined volume of water is that volume estimated to be permitted to flow through the treatment system following the refurbishing activity and before the physical characteristic of the water becomes unacceptable.

13. The method of claim 12 wherein the first signal is an electrical signal and the physical characteristic is conductivity.

14. The method of claim 13 wherein the call based upon the actual physical characteristic is initiated following the expiration of an interval of time during which (a) the actual physical characteristic is continuously detected to be at least equal to the predetermined physical characteristic and (b) water flows continuously through the treatment system.

15. A method for monitoring a water treatment system including:

generating a first signal representing the rate at which water flows through a treatment system subsequent to a defined event;

generating a second signal representing a physical characteristic of the water;

computing the total volume of water which has flowed through the treatment system subsequent to the defined event;

computing the elapsed time interval from the occurrence of the defined event;

initiating a call to a central computer system upon the occurrence of any one of the following events:

a) if the total volume of water computed to have flowed through the treatment system subsequent to the defined event becomes equal to a predetermined volume of water;

b) if the physical characteristic represented by the second signal becomes equal to a predetermined physical characteristic and the first signal is coincidentally being generated;

c) if the actual time interval which has elapsed from the defined event becomes equal to a predetermined time interval.

16. The method of claim 15 wherein the call is initiated upon the first to occur of any one of the said following events.

17. The method of claim 16 wherein the call is initiated when the actual elapsed time interval becomes equal to an integer multiple of the predetermined time interval.

* * * * *

UNITED STATES PATENT AND TRADEMARK OFFICE

CERTIFICATE OF CORRECTION

PATENT NO. : 5,058,032

DATED : October 15, 1991

INVENTOR(S) : Michael D. Farrell, Terry F. Teach and John N. Evers

It is certified that error appears in the above-identified patent and that said Letters Patent is hereby corrected as shown below:

In column 2, line 68 after "computer" insert a --.--.

In column 10, line 13, after "replacement" insert a --.--.

Col. 27, claim 10, line 49, after "treatment" insert --system--.

Columns 27 and 28 are duplicated in the patent, delete the second reference to columns 27 and 28.

Signed and Sealed this

Ninth Day of March, 1993

*Attest:*

STEPHEN G. KUNIN

*Attesting Officer*

*Acting Commissioner of Patents and Trademarks*